United States Patent [19]

Kamboj et al.

[11] Patent Number: 5,494,792
[45] Date of Patent: Feb. 27, 1996

[54] KAINATE-BINDING, HUMAN CNS RECEPTORS OF THE EAA2 FAMILY

[75] Inventors: Rajender Kamboj, Mississauga; Stephen L. Nutt, Etobicoke; Lee Shekter, Toronto; Michael A. Wosnick, Thornhill, all of Canada

[73] Assignee: Allelix Biopharmaceuticals Inc., Mississauga, Canada

[21] Appl. No.: 91,569

[22] Filed: Jul. 15, 1993

Related U.S. Application Data

[62] Division of Ser. No. 750,081, Aug. 27, 1991, abandoned.

[51] Int. Cl.$^6$ ............................ C12N 5/10; C12N 15/10; C12Q 1/00; G01N 33/50
[52] U.S. Cl. .................. 435/4; 435/69.1; 435/240.2; 436/501; 530/350
[58] Field of Search ........................ 435/69.1, 172.3, 435/240.2, 320.1, 4, 7.21; 530/350; 436/501

[56] References Cited

PUBLICATIONS

Egebjerg, J. et al. *Nature* 351:745–749 (1991).
Wada, K. et al. *Nature* 342:684–689 (1989).
Werner, P. et al. *Nature* 351:742–744 (1991).
Bochet, P. et al. in *Comparative Molecular Neurobiology*, ed. by Y. Pideon, pp. 224–231. (1993).
Bowie, D. et al., *British Journal of Pharmacology* 111(3):803–810 (1994).

*Primary Examiner*—Keith C. Furman
*Assistant Examiner*—Dian Jacobson
*Attorney, Agent, or Firm*—Foley & Lardner

[57] ABSTRACT

Neurotransmission by excitatory amino acids (EAAs) such as glutamate is mediated via membrane-bound surface receptors. DNA coding for one family of these receptors, of the kainate binding type of EAA receptors, has now been isolated and the receptor protein characterized. Herein described are recombinant cell lines which produce the EAA receptor as a heterologous membrane-bound product. Also described are related aspects of the invention, which are of commerical significance. Included is use of the cell lines as a tool for discovery of compounds which modulate EAA receptor stimulation.

2 Claims, 22 Drawing Sheets

FIG. 1(A-1)

```
     EcoRI
      |
   1  GAATTCCGGCCCTGTGGACTGCCCTCTCCCCCGCCCCACCACCCAGCGCCA    60
      CTTAAGGCCGGGACACCTGACGGGAGAGGGGGCGGGGTGGTGGGTCGCGGT

BamHI
                                                   |
  61  GAGCCACCTCCCCGCTGTCTGCGGGTCTCGAGGGAGCCAGCCCTCCCACCAG   120
      CTCGGTGGAGGGGCGACAGCCCAGAGCTCCCTCGGTCGGGAGGGTGGGTC

SacII
                  |
 121  GATCCGTGGCGAGTGGGCCCGGCAGCTGCTCCCCATGAGGAGGAAGATGCC   180
      CTAGGCACCGCTCACCCGGGCCGTCGACGAGGGGTACTCCTCCTTCTACGG

M   P
                                                   -18
 181  GGCTGAGCTGCTGCTGCTGATTGTTGCCTTCGCCCAGCTGCCAGGTGCTCTC   240
      CCGACTCGACGACGACGACTAACAACGGAAGCGGGTCGACGGTCCACGAGAG

A   E   L   L   L   L   I   V   A   F   A   S   P   S   C   Q   V   L   S      4
         -15                      -10                      -5                   |
                                                                                |_Mature N-terminal
```

FIG. I(A-2)

```
                                                           SacII
241  ATCACTGGCGCATGGCTGCAATCCCTGGATGATCAGATGTGTGGCCGCGGTGAGCGTCT
     --------+---------+---------+---------+---------+---------+  300
     TAGTGACCGCGTACCGACGTTAGGGACCTACTAGTCTGTCACACACCGGCGCCACTCGCAGA

5    S  L  R  M  A  A  I  L  D  D  Q  T  V  C  G  R  G  E  R  L   24

301  GGCCTTGGCCCTTGGCCCCGGGAGCAGATCAACGGGATCATCGAGGTCCCAGCCAAGGCCCG
     --------+---------+---------+---------+---------+---------+  360
     CCGGAACCGGGAACCGGGGCCCTCGTCTAGTTGCCCTAGTAGCTCCAGGGTCGGTTCCGGGC

25    A  L  A  R  E  Q  I  N  G  I  I  E  V  P  A  K  A  R   44
                                              PstI

361  AGTGGAAGTAGACATCTTTGAGCTGCAGCGGGACAGCCAGTACGAGACCACGGACACCAT
     --------+---------+---------+---------+---------+---------+  420
     TCACCTTCATCTGTAGAAACTCGACGTCGCCCTGTCGGTCATGCTCTGGTGCCTGTGGTA

45    V  E  V  D  I  F  E  L  Q  R  D  S  Q  Y  E  T  T  D  T  M   64

421  GTGTCAGATCTTACCCAAAGGGGTTGTGTCTGTGTCCTTGGGCCCTCCTAGCCCAGCATC
     --------+---------+---------+---------+---------+---------+  480
     CACAGTCTAGAATGGGTTTCCCAACACAGACAGGAACCCGGGAGGATCGGGTCGTAG

```
481  TGCCTCCACCGTGAGCCATATCTGTGGAGAGAAGGAGATCCCCCACATCAAGGTGGGTCC
     ----+----|----+----|----+----|----+----|----+----|----+----|  540
     ACGGAGGTGGCACTCGGTATAGACACCTCTCTTCCTCTAGGGGGTGTAGTTCCACCCAGG

A  S  T  V  S  H  I  C  G  E  K  E  I  P  H  I  K  V  G  P
 85                                                                104

541  CGAGGAGACACCCCGCCTTCAGTACCTTCGCTTCGCGTCTGTCAGCCTGTACCCCAGTAA
     ----+----|----+----|----+----|----+----|----+----|----+----|  600
     GCTCCTCTGTGGGGCGGAAGTCATGGAAGCGAAGCGCAGACAGTCGGACATGGGGTCATT

E  E  T  P  R  L  Q  Y  L  R  F  A  S  V  S  L  Y  P  S  N
105                                                                124

601  CGAGGACGTCAGCTTGGCGGTCTCCCGAATCCTCAAGTCCTTCAACTACCCCTCGGCCAG
     ----+----|----+----|----+----|----+----|----+----|----+----|  660
     GCTCCTGCAGTCGAACCGCCAGAGGGCTTAGGAGTTCAGGAAGTTGATGGGGAGCCGGTC

E  D  V  S  L  A  V  S  R  I  L  K  S  F  N  Y  P  S  A  S
125                                                                144

661  CCTCATCTGCGCCAAGGCTGAGTGCCTGCTGCGATTGGAGGAACTGGTGCGTGGCTTCCT
     ----+----|----+----|----+----|----+----|----+----|----+----|  720
     GGAGTAGACGCGGTTCCGACTCACGGACGACGCTAACCTCCTTGACCACGCACCGAAGGA

L  I  C  A  K  A  E  C  L  L  R  L  E  E  L  V  R  G  F  L
145                                                                164

721  CATCTCCAAGGAGACGCTGTCAGTGAGGATGTTGGACGACAGCCGGGACCCCACACCACT
     ----+----|----+----|----+----|----+----|----+----|----+----|  780
     GTAGAGGTTCCTCTGCGACAGTCACTCCTACAACCTGCTGTCGGCCCTGGGGTGTGGTGA
```

FIG. I(B-2)

```
165  I   S   K   E   T   L   S   V   R   M   L   D   D   S   R   D   P   T   P   L   184
781  GCTCAAGGAGATCCGTGATGACAAGGTGTCCACCATCATCGACGCCAACGCCTCCAT  840
     CGAGTTCCTCTAGGCACTACTGTTCCACAGGTGGTAGTAGTAGCTGCGGTTGCGGAGGTA

185  L   K   E   I   R   D   D   K   V   S   T   I   I   I   D   A   N   A   S   I   204
841  CTCCCCACCTCATCCTCCGTAAGGCCTCGGAACTGGGAATGACCCTCAGCGTTTTACAAGTA  900
     GAGGGTGGAGTAGGAGGCATTCCGGAGCCTTGACCCTTACTGGGAGTCGCAAAATGTTCAT

205  S   H   L   I   L   R   K   A   S   E   L   G   M   T   S   A   F   Y   K   Y   224
                              NcoI
901  CATCCTCACCATGGACTTCCCCATCCTGGACGGTATTGTGGAGGACTCCTC  960
     GTAGGAGTGGTACCTGAAGGGGTAGGACGTAGACCTGCCATAACACCTCCTGAGGAG

225  I   L   T   T   M   D   F   P   I   L   H   L   D   G   I   V   E   D   S   S   244
961  CAACATCCTGGGCTTCTCCATGTTCAACACGTCCCACCCCTTCTACCCTGAGTTTGTCCG  1020
     GTTGTAGGACCCGAAGAGGTACAAGTTGTGCAGGGTGGGAAGATGGGACTCAAACAGGC

```
1021  CAGCCCTCAACATGTCCTGGAGGGAGAACTGTGAAGCCAGCACCTACCTGGGCCCTGCGCT
      ----------+---------+---------+---------+---------+---------+  1080
      GTCGGAGTTGTACAGGACCTCCCTCTTGACACTTCGGTCGTGGATGGACCCGGGACGCGA

265    S  L  N  M  S  W  R  E  N  C  E  A  S  T  Y  L  G  P  A  L   284

1081  GTCAGCCGCGCCCTGATGTTTGACGCCGTGCACGTGGTGAGCGCTGTCCGAGAGCTGAA
      ----------+---------+---------+---------+---------+---------+  1140
      CAGTCGGCGCGGGACTACAAACTGCGGCACGTGCACCACTCGCGACAGGCTCTCGACTT

285    S  A  A  L  M  F  D  A  V  H  V  V  S  A  V  R  E  L  N   304

1141  CCGCAGCCAGGAGATCGGTGTGAAGCCTCTGGCCTGTACATCGGCCAACATTTGGCCCCA
      ----------+---------+---------+---------+---------+---------+  1200
      GGCGTCGGTCCTCTAGCCACACTTCGGAGACCGGACATGTAGCCGGTTGTAAACCGGGGT

305    R  S  Q  E  I  G  V  K  P  L  A  C  T  S  A  N  I  W  P  H   324

1201  CGGGACCAGCCTCATGAACTACCTGCGCCATGGTAGAGTATCATGGCTGACCGGGGCGGGT
      ----------+---------+---------+---------+---------+---------+  1260
      GCCCTGGTCGGAGTACTTGATGGACGCGGTACCATCTCATAGTACCGACTGGCCCCGCCCA

325    G  T  S  L  M  N  Y  L  R  M  V  E  Y  D  G  L  T  G  R  V   344

1261  CGAGTTCAACAGCAAAGGGCAGAGAACCAACTACACACCCTGGCGCATCCTAGAAAAGTCCCG
      ----------+---------+---------+---------+---------+---------+  1320
      GCTCAAGTTGTCGTTTCCCGTCTCTTGGTTGATGTGGACCGCGTAGGATCTTTTCAGGGC
```

FIG. I(C-2)

```
345   E  F  N  S  K  G  Q  R  T  N  Y  T  L  R  I  L  E  K  S  R   364
1321  GCAGGGCCACCGTGAGATTGGGGTACTCTAACCGCACCCTGGCCATGAATGCCAC  1380
      --------+---------+---------+---------+---------+---------+
      CGTCCCGGTGGCACTCTAACCCCATGAGATTGGCGTGGGACCGGTACTTACGGTG

365   Q  G  H  R  E  I  G  V  W  Y  S  N  R  T  L  A  M  N  A  T   384
1381  CACCCTGGACACATCAACCTGTCGCAGACACTGGCCAACAAGACCCTGGTCACAACCAT  1440
      --------+---------+---------+---------+---------+---------+
      GTGGGACCTGTAGTTGGACAGCGTCTGTGACCGGTTGTTCTGGGACCACCAGTGTTGGTA

385   T  L  D  I  N  L  S  Q  T  L  A  N  K  T  L  V  V  T  T  I   404
1441  CCTGGAGAACCCATACGTCATGCGCCGGCCCAACTTCCAGGGCCTGTCGGGGAACGAACG  1500
      --------+---------+---------+---------+---------+---------+
      GGACCTCTTGGGTATGCAGTACGCGGCCGGGTTGAAGGTCCCGGACAGCCCCTTGCTTGC

405   L  E  N  P  Y  V  M  R  R  P  N  F  Q  G  L  S  G  N  E  R   424
1501  CTTCGAGGGCTTCTGCGTGGACATGCTGCGGCCCAGCTGCCTGCTGCCGTTCCCGTA  1560
      --------+---------+---------+---------+---------+---------+
      GAAGCTCCCGAAGACGCACCTGTACGACGCCCGGGCTCGACGGCAAGGGCAT

```
561   CCGCCTGCGGGTTGGTGGAGGATGGGCTGTACGGGGCGCCCGAGCCCAAGGGCTCCTGGAC
      ----+----|----+----|----+----|----+----|----+----|----+----| 1620
      GGCGGACGCCAACCACCTCCTACCCGACATGCCCCGCGGGCTCGGGTTGCCGAGGACCTG

445   R   L   R   L   V   E   D   G   L   Y   G   A   P   E   P   N   G   S   W   T   464
                                    SacI

1621  GGGCATGGTTGGCGAGCTGATCAACCGGAAGGCAGACCTGGCTGTGGCCGCCTTCACCAT
      ----+----|----+----|----+----|----+----|----+----|----+----| 1680
      CCCGTACCAACCGCTCGACTAGTTGGCCTTCCGTCTGGACCGACACCGGCGGAAGTGGTA

465   G   M   V   G   E   L   I   N   R   K   A   D   L   A   V   A   A   F   T   I   484

1681  CACAGCTGAGCGGGAGAAGGTCATCGACTTTTCCAAGCCCTTTATGACCCTGGGGATCAG
      ----+----|----+----|----+----|----+----|----+----|----+----| 1740
      GTGTCGACTCGCCCTCTTCCAGTAGCTGAAAAGGTTCGGGAAATACTGGGACCCCTAGTC

485   T   A   E   R   E   K   V   I   D   F   S   K   P   F   M   T   L   G   I   S   504

1741  CATCCTCTACCGAGTGCACATGGGCCGCAAGCCTGGCTACTTCTCCCTTCCTGGACCCTT
      ----+----|----+----|----+----|----+----|----+----|----+----| 1800
      GTAGGAGATGGCTCACGTGTACCCGGCGTTCGGACCGATGAAGAGGAAGGACCTGGGGAA

505   I   L   Y   R   V   H   M   G   R   K   P   G   Y   F   S   F   L   D   P   F   524

1801  CTCCCCTGTCTGTGGCTCTTCATGCTTCTTGCCTACCTGGCTGTCAGCTGCTCCTGTT
      ----+----|----+----|----+----|----+----|----+----|----+----| 1860
      GAGGGGACACACCGAGAAGTACGAAGAACGGATGGACCGACAGTCGACGAGGACAA
```

FIG. I(D-2)

```
525   S   P   A   V   W   L   F   M   L   L   A   Y   L   A   V   S   C   V   L   F   544
      TCTGGCTGCCAGGCTGAGCCCCTATGAGTGGTATAACCCACACCCATGCCTGCGGGCACG
1861  ------+---------+---------+---------+---------+---------+   1920
      AGACCGACGGTCCGACTCGGGGATACTCACCATATTGGGTGTGGTACGGACGCCCGTGC

545   L   A   A   R   L   S   P   Y   E   W   Y   N   P   H   P   C   L   R   A   R   564
      CCCCCACATCCTGGAGAACCAGTACACGCTGGGCAACAGCCTGTGGTTTCCCGTGGGGGG
1921  ------+---------+---------+---------+---------+---------+   1980
      GGGGGTGTAGGACCTCTTGGTCATGTGCGACCCGTTGTCGGACACCAAAGGGCACCCCCC

565   P   H   I   L   E   N   Q   Y   T   L   G   N   S   L   W   F   P   V   G   G   584
      CTTCATGCAGCAGGGCTCGGAGATCATGCCCCGGGCTCTGTCCACGCGCTGTGTCAGCGG
1981  ------+---------+---------+---------+---------+---------+   2040
      GAAGTACGTCGTCCCGAGCCTCTAGTACGGGGCCCGAGACAGGTGCGCGACACAGTCGCC

585   F   M   Q   Q   G   S   E   I   M   P   R   A   L   S   T   R   C   V   S   G   604
      AGTCTGGTGGGCCTTCACCTTGATCATCTCCTACGGCCAACCTGGCCGGCCTT
2041  ------+---------+---------+---------+---------+---------+   2100
      TCAGACCACCCGGAAGTGGAACTAGTAGAGGAGGATGTGCCGGTTGGACCGGCCGGAA

```
2101  CCTCACCGTGCAGCGGCCATGGAGGTGCCTGTGGAGTCGGCCGATGACCTGGCCGATCAGAC
      ------+---------+---------+---------+---------+---------+  2160
      GGAGTGGCACGTCGCCGGTACCTCCACGGACACCTCAGCCGGCTACTGGACCGTCTAGTCTG

625   L  T  V  Q  R  M  E  V  P  V  E  S  A  D  D  L  A  D  Q  T   644

EcoRI
2161  CAACAATCGAGTATGGCACCATCCACGCCGGCTCCACCATGACCTTCTTCCAGAATTCACG
      ------+---------+---------+---------+---------+---------+  2220
      GTTGTAGCTCATACCGTGGTAGGTGCGGCCGAGGTGGTACTGGAAGAAGGTCTTAAGTGC

645   N  I  E  Y  G  T  I  H  A  G  S  T  M  T  F  F  Q  N  S  R   664

KpnI
2221  GTACCAAACGTACCAGCGCATGTGGAACTACATGCAGTCGAAGCAGCCCAGCGTGTTCGT
      ------+---------+---------+---------+---------+---------+  2280
      CATGGTTTGCATGGTCGCGTACACCTTGATGTACGTCAGCTTCGTCGGGTCGCACAAGCA

665   Y  Q  T  Y  Q  R  M  W  N  Y  M  Q  S  K  Q  P  S  V  F  V   684

2281  CAAGAGCACAGAAGAGGGCATTGCCGCCGTCCTCAACTCCCGCTACGCCTTCCTGCTCGA
      ------+---------+---------+---------+---------+---------+  2340
      GTTCTCGTGTCTTCTCCCGTAACGGCGGCAGGAGTTGAGGGCGATGCGGAAGGACGAGCT

```
2341 GTCCACCATGAACGAATACCACCGGCGGCCTCAACTGCAACCTCACCCAGATCGGGGGACT
     ---------+---------+---------+---------+---------+---------+  2400
     CAGGTGGTACTTGCTTATGGTGGCCGCCGGAGTTGACGTTGGAGTGGGTCTAGCCCCCTGA

705   S  T  M  N  E  Y  H  R  R  L  N  C  N  L  T  Q  I  G  G  L   724
                                                    SphI
2401 CCTCGACACCAAGGGCTACGGCATTGGCATGCCGCTCGGGCTCCCCGTTCCCGGATGAGAT
     ---------+---------+---------+---------+---------+---------+  2460
     GGAGCTGTGGTTCCCGATGCCGTAACCGTACGGCGAGCCCGAGGGGCAAGGCCTACTCTA

725   L  D  T  K  G  Y  G  I  G  M  P  L  G  S  P  F  R  D  E  I   744
                                      PstI
2461 CACAACTGGCCATCCTGCAGCTTCAGGAGAACAACCGGCTGGAGATCCTGAAGCGCAAGTG
     ---------+---------+---------+---------+---------+---------+  2520
     GTGTTGACCGGTAGGACGTCGAAGTCCTCTTGTTGGCCGACCTCTAGGACTTCGCGTTCAC

745   T  L  A  I  L  Q  L  Q  E  N  N  R  L  E  I  L  K  R  K  W   764

2521 GTGGGAGGGGCGGTGCCCCAAGGAGGAGGACCATCGAGCTAAAGGTTTGGGCATGGA
     ---------+---------+---------+---------+---------+---------+  2580
     CACCCTCCCCGCCACGGGGTTCCTCCTCCTGGTAGCTCGATTTCCAAACCCGTACCT

```
2581  GAACATTGGTGGCATTTTTATCGTGCTCATCATTGCTGTGCTTCGTGGC
      ------+---------+---------+---------+---------+---------+  2640
      CTTGTAACCACCGTAAAAATAGCACGAGTAGTAACGACAGAAGCACCG

785    N  I  G  G  I  F  I  V  L  I  I  A  V  F  V  A   804
                        EcoRI

2641  GGTCATGGAATTCATATGGTCCAGCTGAGTCCGAGGAGGTGTCGGTGTG
      ------+---------+---------+---------+---------+---------+  2700
      CCAGTACCTTAAGTATACCAGGTCGACTCAGGCTCCTCCACAGCCACAC

805    V  M  E  F  I  W  S  T  R  R  S  A  E  S  E  E  V  S  V  C   824
                              PstI

2701  CCAGGAGATGCTGCAGGAGCTGCGCCACGCGGTTTCTTGCCGCAAGACGTCGCGTTCCCG
      ------+---------+---------+---------+---------+---------+  2760
      GGTCCTCTACGACGTCCTCGACGCGGTGCGCCAAAGAACGGCGTTCTGCAGCGCAAGGGC

825    Q  E  M  L  Q  E  L  R  H  A  V  S  C  R  K  T  S  R  S  R   844

2761  CCGGCGCCGACGCGGGCCCGGGCCCCTGTCACTGCGGCGGTCCGCGA
      ------+---------+---------+---------+---------+---------+  2820
      GGCCGCGGCTGCGCCCGGGCCCCGGGGCTCGGCGACAGTGACGCCGCCAGGCGCT

```
2821  GATGCGCCTCAGCAACGGCAAGCTCTACTCGGCCGGGGATGCGGGCAGCGC
      ----+----+----+----+----+----+----+----+----+----+  2880
      CTACGCGGAGTCGTTGCCGTTCGAGATGAGCCGGCCCCCTACGCCCGTCGCG

865        M  R  L  S  N  G  K  L  Y  S  A  G  D  A  G  S  A    884

2881  GCACGGGGGCCCGCAGCCCGCCTCCTGGACGACCCGGGCCCCCAGCCCGACCCGC
      ----+----+----+----+----+----+----+----+----+----+  2940
      CGTGCCCCCGGGCGTCGGGCGGAGGACTGCTGGGCCCCGGGGGTCGGGCTGGGCG

885        H  G  P  Q  R  L  D  D  P  G  P  P  S  G  A  R  P  A    904

2941  CGCCCCCACCCCCTGCACCCACGTGCGCGTCTGCCAGGAGTGCCGGCGCATCCAGGCGCT
      ----+----+----+----+----+----+----+----+----+----+  3000
      GCGGGGGTGGGGGACGTGGGTGCACGCGCAGACGGTCCTCACGGCCGCGTAGGTCCGCGA

905        A  P  T  P  C  T  H  V  R  V  C  Q  E  C  R  R  I  Q  A  L    924

3001  GCGGGCCTCGGGGCCCCCGGAGCCCCCGGAGGCCACCGAGGACCCCCAGGGGCGCTTCGGTGGTC
      ----+----+----+----+----+----+----+----+----+----+  3060
      CGCCCGGAGCCCCGGGGGGCCTCGGGGGGCCTCCGGTGGCTCCTGGGGGTCCCCGCGAAGCCACCAG

925        R  A  S  G  A  G  A  P  P  R  G  L  G  V  P  A  E  A  T  S    944
                          SacII

3061  CCCGCCCCCGGCCCGGCCCTGGCCCCGGCCCCGGGGGCGGACCGGTGAGCTGGCGGAGCACGAGTGACC
      ----+----+----+----+----+----+----+----+----+----+  3120
      GGGCGGGGGCCGGGCCGGGACCGGGGCCGGGGCCCCCGCCTGGCCACTCGACCGCCTCGTGCTCACTGG

```
      ACGGGGGGGCTGTGCGGGCGCCCGACTGACCGAAGGGACGGGCCCGCCCCAGGCCCC
3121  ---------+---------+---------+---------+---------+---------+  3180
      TGCCCGCCCCGACACGCCCGACTGGCTTCCCTGCCCGGGCGGGGTCCGGGG

AGCAGTCTCCGCTCCCGCAGCGGGGACAGGACTTGTGCGCGGCCCCGACGC
3181  ---------+---------+---------+---------+---------+---------+  3240
      TCGTCAGAGGCGAGGGCGTCGCCCGCCCTGTCCTGAACACGCGCCGGGGCCTGCG

CGGCGATTTTGCCCTTTGGTTCCCCGCGAAGTCCGAGGCCTGGCTCTGAGCCCGCTGCGC
3241  ---------+---------+---------+---------+---------+---------+  3300
      GCGCTAAAACGGAAACCAAGGGGCGCTTCAGGCTCCGGACCCGAGACCTCGGGCGACGCG
                                           SacII
                                           |

CCCCCAGTCGGACTCGCGGCGGGCTGCGGAGAAGGGCGCAGGAACCGAGGACTCC
3301  ---------+---------+---------+---------+---------+---------+  3360
      GGGGGTCACCTGAGCGCCGCTCTCCCGCGTCCTTCCCGCGTCCTTGGCTCCTGAGG

AGGGGCTGGGACTTCGGGCGGGCTCTGGGCGAAAGCAGTCAGCGGGAGAGGACCC
3361  ---------+---------+---------+---------+---------+---------+  3420
      TCCCCGACCCTGAAGCCCGCCGAGACCCCTTCGCCTTCGTCAGTCGCCTCCCTGGG
```

FIG. 1(G-2)

```
      CATTCTGGGACTGCTCAGGCTCCCCAAGACTTGACGCAGCCCCCACGCTTCTGAGGTGG
3421  ------+---------+---------+---------+---------+---------+   3480
      GTAAGACCCTGACGAGTCCGAGGGGTTCTGAACTGCGTCGGGGGTGCGAAGACTCCACC

GGAGGGCCTCTGGACAGATGGGTGTCCCCTGGTGCCCCTCCACTCTTCTCTTCCTCTCTT
3481  ------+---------+---------+---------+---------+---------+   3540
      CCTCCCGGAGACCTGTCTACCCACAGGGGACCACGGGGAGGTGAGAGAAGAGAGAGAA

TTTTGGGGGAGAAACCTCGGAATTTCTATGAGACCCTCCCCCAGGGAGGGGGTCAGTTGG
3541  ------+---------+---------+---------+---------+---------+   3600
      AAAACCCCCTCTTTGGAGCCTTAAAGATACTCTGGAGGGGTCCCCCAGTCAACC

GCCCCCATCCCCCTTGCCACATCGCAGCCCCTGTTGGAATAAAAAAAGAACAAAAG
3601  ------+---------+---------+---------+---------+---------+   3660
      CGGGGGTAGGAGGGGAACGGTGTAGCCGTCGGGGACAACCCTTATTTTTTTCTTGTTTTC

EcoRI
                                              |
      GGGAAAAAAAAAAAAAAAAAAAAAAAAAAAAAAAGGAATTC
3661  ------+---------+---------+------   3695
      CCCTTTTTTTTTTTTTTTTTTTTTTTTTTTTTTTCCTTAAG
```

FIG. 4(A)

```
          466  MetValGlyGluLeuIleAsnArgGlnLysAlaAspLeuLeuAlaValAla       481
Hum EAA2b 1625 ATGGTTGGCGAGCTCATCAACCGGCAGAAGGCAGAACCTGGCTGTGGCC       1672
               |||||||||||||||||||||||||   |||||   ||||||||||||||
Hum EAA2a 1625 ATGGTTGGCGAGCTCATCAACCGG...AAGGCAGACCTGGCTGTGGCC       1669
          466  MetValGlyGluLeuIleAsnArg...LysAlaAspLeuLeuAlaValAla       480
```

FIG. 4(B)

```
Hum EAA2a    226  CTGCCAGGTGCTCTCATCACTGCGCATGGCTGCAATCCTGGATGATCAGA  275
                                                 ||| |    |  |  |
Hum EAA2c      8  ............................GGATGAGGCACAAGAATCACTTGGACCGG   36

HumEAA2a     276  CAGTGTGTGGCCGGGTGAGCGTCTGGCCTTGGCCCGGGAGCAG         325
                     || |  |  ||||  |||||||||||||||||||||||||
HumEAA2c      37  GAGGCAGGAGTTGCAGTGAGCGTCTGGCCTTGGCCCCGGGAGCAG        86
```

---

```
                     |-Signal Peptide-||-Mature N-Terminal
Hum EAA2a     1  MPAELLLLLIVAFASPSCQVLSSLRMAAILDDQTVCGRGERLALALA          29
                   |. : ....: ::|||||||||
Hum EAA2c     1  ............................DEAQESLGPGGRSCSERLALALA     23

Hum EAA2a    30  REQINGIIEVPAKARVEVDIFELQRDSQYETTDTMCQIILPK              70
                 |||||||||||||||||||||||||||||||||||||||||
Hum EAA2c    24  REQINGIIEVPAKARVEVDIFELQRDSQYETTDTMCQIILPK              64
```

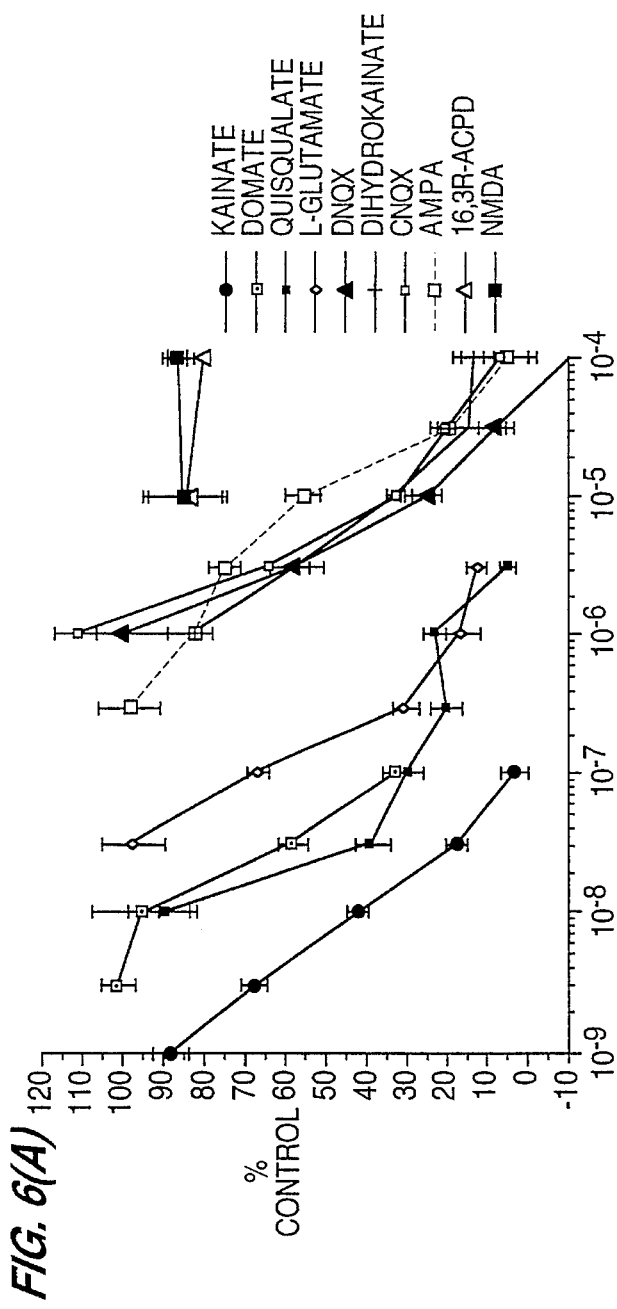

KAINATE-BINDING, HUMAN CNS RECEPTORS OF THE EAA2 FAMILY

This application is a division of application Ser. No. 07/750,081, filed Aug. 27, 1991, now abandoned.

BACKGROUND OF THE INVENTION

Field of the Invention

This invention is concerned with applications of recombinant DNA technology in the field of neurobiology. More particularly, the invention relates to the cloning and expression of DNA coding for excitatory amino acid (EAA) receptors, especially human EAA receptors.

In the mammalian central nervous system (CNS), the transmission of nerve impulses is controlled by the interaction between a neurotransmitter substance released by the "sending" neuron and a surface receptor on the "receiving" neuron. L-glutamate is the most abundant neurotransmitter in the CNS, and mediates the major excitatory pathway in vertebrates. Glutamate is therefore referred to as an excitatory amino acid (EAA) and the receptors which respond to it are variously referred to as glutamate receptors, or more commonly as EAA receptors.

Using tissues isolated from mammalian brain, various synthetic EAA receptor agonists, knowledge of EAA receptor pharmacology has been refined somewhat. Members of the EAA receptor family are now grouped into three main types based on differential binding to such agonists. One type of EAA receptor, which in addition to glutamate also binds the agonist NMDA (N-methyl-D-aspartate), is referred to as the NMDA type of EAA receptor. Two other glutamate-binding types of EAA receptor, which do not bind NMDA, are named according to their preference for binding with two other EAA receptor agonists, namely AMPA (alpha-amino-3-hydroxy- 5-methylisoxazole-4-propionate), and kainate. Particularly, receptors which bind glutamate but not NMDA, and which bind with greater affinity to kainate than to AMPA, are referred to as kainate type EAA receptors. Similarly, those EAA receptors which bind glutamate but not NMDA, and which bind AMPA with greater affinity than kainate are referred to as AMPA type EAA receptors.

The family of glutamate-binding EAA receptors is of great physiological and medical importance. Glutamate is involved in many aspects of long-term potentiation (learning and memory), in the development of synaptic plasticity, in epileptic seizures, in neuronal damage caused by ischemia following stroke or other hypoxic events, as well as in other forms of neurodegenerative processes. However, the development of therapeutics which modulate these processes has been very difficult, due to the lack of any homogeneous source of receptor material with which to discover selectively binding drug molecules, which interact specifically at the interface of the EAA receptor. The brain derived tissues currently used to screen candidate drugs are heterogeneous receptor sources, possessing on their surface many receptor types which interfere with studies of the EAA receptor/ligand interface of interest. The search for human therapeutics is further complicated by the limited availability of brain tissue of human origin. It would therefore be desirable to obtain cells that are genetically engineered to produce only the receptor of interest. With cell lines expressing cloned receptor genes, a substrate which is homogeneous for the desired receptor is provided for drug screening programs.

Very recently, genes encoding substituent polypeptides of EAA receptors from non-human sources, principally rat, have been discovered. Hollmann et al., Nature 342: 643, 1989 described the isolation from rat of a gene referred to originally as GluR-K1 (but now called simply GluR1). This gene encodes a member of the rat EAA receptor family, and was originally suspected as being of the kainate type. Subsequent studies by Keinanen et al., Science 249: 556, 1990, showed, again in rat, that a gene called GluR-A, which was in fact identical to the previously isolated GluR1, in fact encodes a receptor not of the kainate type, but rather of the AMPA type. These two groups of researchers have since reported as many as five related genes isolated from rat sources. Boulter et al., Science 249: 1033, 1990, revealed that, in addition to GluR1, the rat contained 3 other related genes, which they called GluR2, GluR3, and GluR4, and Bettler et al., Neuron 5: 583, 1990 described GluR5. Keinanen et al., supra, described genes called GluR-A, GluR-B, GluR-C and GluR-D which correspond precisely to GluR1, GluR2, GluR3 and GluR4 respectively, Sommer et al., Science 249: 1580, 1990 also showed, for GluR-A, GluR-B, GluR-C and GluR-D two alternatively spliced forms for each gene. These authors, as well as Monyer et al, Neuron 6:799, 1991 were able to show that the differently spliced versions of these genes were differentially expressed in the rat brain. In addition to the isolation of these AMPA receptor genes, several studies have more recently attempted to determine the ion-gating properties of different mixtures of the known receptors (Nakanishi et al., Neuron 5: 569, 1990; Hollmann et al., Science 252: 851, 1991; Verdoorn et al., Science 252: 1715, 1991; and see WO 91/06648).

Some recent work has also been published regarding non-human genes which appear to encode the kainate-type of receptor. Egebjerg et al., Nature 351: 745, 1991, have described the isolation of a gene from rat called GluR6, which although related in sequence to the AMPA receptor genes, forms a receptor which is not activated by AMPA but rather by glutamate, quisqualate, and preferentially, kainate. Other kainate-binding proteins have been described from frog (Wada et al., Nature 342: 684, 1989), chicken (Gregor et al., Nature 342: 689, 1989) and from rate (Werner et al., Nature 351: 742, 1991). These latter genes encode proteins which bind kainate, but which do not readily form into functional ion channels when expressed by themselves.

There has emerged from these molecular cloning advances a better understanding of the structural features of EAA receptors and their subunits, as they exist in the rat brain. According to the current model of EAA receptor structure, each is heteromeric in structure, consisting of individual membrane-anchored subunits, each having four transmembrane regions, and extracellular domains that dictate ligand binding properties to some extent and contribute to the ion-gating function served by the receptor complex. Keinanen et al., supra, have shown for example that each subunit of the rat GluR receptor, including those designated GluR-A, GluR-B, GluR-C and GluR-D, display cation channel activity gated by glutamate, by AMPA and by kainate, in their unitary state. When expressed in combination however, for example GluR-A in combination with GluR-B, gated ion channels with notably larger currents are produced by the host mammalian cells.

In the search for therapeutics useful to treat CNS disorders in humans, it is highly desirable of course to provide a screen for candidate compounds that is more representative of the human situation than is possible with the rat receptors isolated to date. It is particularly desirable to provide cloned genes coding for human receptors, and cell lines expressing those genes, in order to generate a proper screen for human therapeutic compounds. These, accordingly are objects of the present invention.

It is another object of the present invention to provide, in isolated form, a DNA molecule which codes for a human EAA receptor.

It is another objects of the present invention to provide a cell that has been genetically engineered to produce a kainate-binding human EAA receptor.

Other object of the present invention will be apparent from the following description of the invention.

SUMMARY OF THE INVENTION

Genes coding for a family of EAA receptors endogenous to human brain have now been identified and characterized. A representative member of this human EAA receptor family, designated human EAA2a, codes for a receptor protein that in addition to binding glutamate with an affinity typical of EAA receptors, also exhibits ligand binding properties characteristic of kainate-type EAA receptors. Sequence-related genes coding for naturally occurring variants of the human EAA2a receptor have also been identified, and constitute additional members of this receptor family, herein referred to as the human EAA2 receptor family.

The present invention thus provides, in one of its aspects, an isolated polynucleotide, consisting either of DNA or of RNA, which codes for a human EAA2 receptor or for a kainate-binding fragment thereof.

In another aspect of the present invention, there is provided a cell that has been genetically engineered to produce a kainate-binding, human EAA receptor belonging to the herein-defined EAA2 family. In related aspects of the present invention, there are provided recombinant DNA constructs and relevant methods useful to create such cells.

In another aspect of the present invention, there is provided a method for evaluating the affinity of a selected compound for binding to a receptor having the characteristics of a human EAA2 receptor, which comprises the steps of incubating the compound with a genetically engineered cell of the present invention, or with a membrane preparation derived therefrom, in a manner suitable to determine the receptor binding affinity of the test compound.

Other aspects of the present invention, which encompasses various applications of the discoveries herein described, will become apparent from the following detailed description, and from the accompanying drawings.

BRIEF DESCRIPTION OF THE DRAWINGS

FIG. 1 provides the nucleotide sequence (SEQ ID. NO. 1) of DNA coding for an excitatory amino acid receptor of the present invention, and the deduced amino acid sequence thereof (SEQ ID. NO. 2);

FIGS. 5 and 6 illustrate graphically the ligand-binding properties of the EAA receptor expressed from the coding region provided in FIG. 1.

DETAILED DESCRIPTION OF THE PREFERRED EMBODIMENTS

The invention relates to excitatory amino acid (EAA) receptors of human origin, and is directed more particularly to a novel family of kainate-type human EAA receptors, herein designated the human EAA2 receptor family. As used herein, the term "human EAA2 receptor" is intended to embrace the human EAA2a receptor, and kainate-binding variants of the EAA2a receptor that are structurally related thereto, i.e. have at least 95% homology therewith, including naturally occurring and synthetically derived variants of the EAA2a receptor. Naturally occurring variants of the human EAA2a receptor include particularly the receptors herein designated human EAA2b receptor, and human EAA2c receptor. As used herein, the term "kainate-binding" refers to receptor variants and receptor fragments that display greater binding affinity for kainate than for either glutamate, AMPA or NMDA, as determined in assays of conventional design, such as the assays herein described.

The particular human EAA receptor designated EAA2a is a protein characterized structurally as a single polypeptide chain that is produced initially in precursor form bearing an 18 residue N-terminal signal peptide, and is transported to the cell surface in mature form, lacking the signal peptide and consisting of 962 amino acids arranged in the sequence illustrated by single letter code in FIG. 1. Unless otherwise stated, amino acid residues of the EAA2a receptor are numbered with reference to the mature protein sequence. With respect to structural domains of the receptor, hydropathy analysis reveals four putative transmembrane domains, one spanning residues 528–547, inclusive, (TM-1), another spanning residues 572–590 (TM-2), a third spanning residues 601–619 (TM-3) and the fourth spanning residues 786–806 (TM-4). Based on this assignment, it is likely that the human EAA2 receptor structure, in its natural membrane-bound form, consists of a 527 amino acid N-terminal extracellular domain, followed by a hydrophobic region containing four transmembrane domains and an extracellular, 156 amino acid C-terminal domain.

Figure 4C:
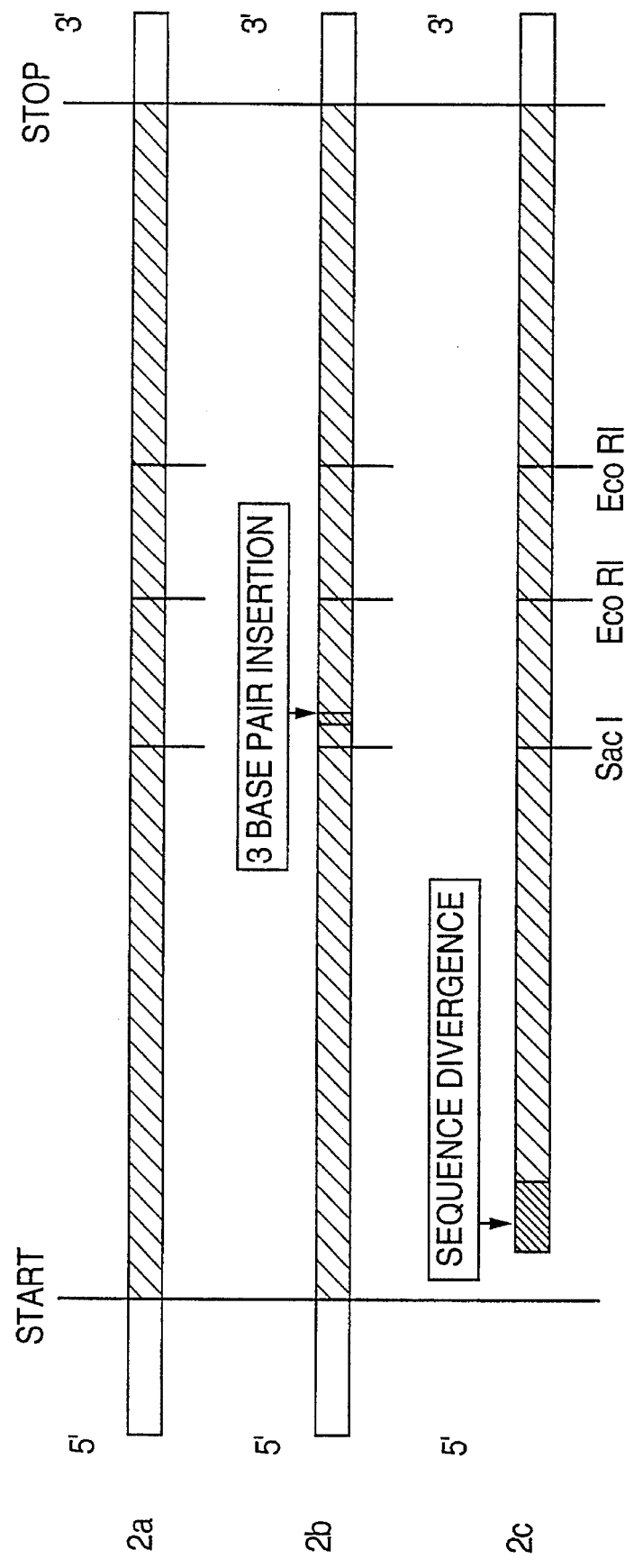
FIGS. 4(1) (SEQ ID. NO. 13–18), 4(2) (SEQ ID. NO. 19–22) and 4(3) show, with reference to FIG. 1, the DNA and amino acid sequences of naturally occurring variants of the EAA receptor illustrated in FIG. 1.

As shown in FIG. 4, structurally related variants of the EAA2a receptor, which occur naturally in human brain tissue, have also been identified. As deduced from nucleotide sequences of the genes coding for them, these variants differ structurally therefrom by the insertion of one additional amino acid between positions 473 and 474 of EAA2a, in the case of EAA2b. Another variant, designated EAA2c, differs from EAA2a by fifteen amino acids in the N-terminal region (FIG. 4). A further variant, designated EAA2d, differs from EAA2a also in the N-terminal region, and has a seven amino acid deletion (FIG. 4).

In human hippocampal cDNA libraries, the source from which DNA coding for the EAA2 receptor was isolated, the EAA2a receptor is encoded by the nucleotide sequence provided in FIG. 1. Relative to nucleic acid sequences that code for excitatory amino acid receptors discovered in rat tissue, as described in the publications mentioned hereinabove, the human EAA2a receptor shares limited nucleic acid sequence identity, at best approximately 60%. This vast structural difference suggests that non-human counterparts of EAA2a remain to be discovered, or perhaps are non-existent.

Like other members of the human EAA2 receptor family, receptor subtype EAA2a is characterized by a pharmacological profile, i.e. a ligand binding "signature", that points strongly to a kainate-type pharmacology, as distinct from other excitatory amino acid receptor types, such as NMDA and AMPA. Despite the understanding that kainate binding receptors require a multi- and perhaps heteromeric subunit structure to function in the pharmacological sense, it has been found that cells producing the unitary EAA2a receptor do, independently of association with other receptor subunits, provide a reliable indication of excitatory amino acid binding. Thus, in a key aspect of the present invention, the human EAA2a receptor is exploited for the purpose of screening candidate compounds for the ability to compete with endogenous EAA receptor ligands and known synthetic analogues thereof for EAA receptor binding.

For use in receptor binding assays, it is desirable to construct by application of genetic engineering techniques a mammalian cell that produces the EAA2a receptor in functional form as a heterologous product. The construction of such cell lines is achieved by introducing into a selected host cell a recombinant DNA construct in which DNA coding for the human EAA2a receptor in a form transportable to the cell surface i.e., bearing its native signal peptide or a functional, heterologous equivalent thereof, is associated with expression controlling elements that are functional in the selected host to drive expression of the receptor-encoding DNA, and thus elaborate the desired EAA2 receptor protein. Such cells are herein characterized as having the receptor-encoding DNA incorporated "expressibly" therein. The receptor-encoding DNA is referred to as "heterologous" with respect to the particular cellular host if such DNA is not naturally found in the particular host. The particular cell type selected to serve as host for production of the human EAA2a receptor can be any of several cell types currently available in the art, but should not of course be a cell type that in its natural state elaborates a surface receptor that can bind excitatory amino acids, and so confuse the assay results sought from the engineered cell line. Generally, such problems are avoided by selecting as host a non-neuronal cell type, and can further be avoided using non-human cell lines, as is conventional. It will be appreciated that neuronal- and human-type cells may nevertheless serve as expression hosts, provided that "background" binding to the test ligand is accounted for in the assay results.

According to one embodiment of the present invention, the cell line selected to serve as host for EAA2 receptor production is a mammalian cell. Several types of such cell lines are currently available for genetic engineering work, and these include the chines hamster ovary (CHO) cells for example of K1 lineage (ATCC CCL 61) including the Pro5 variant (ATCC CRL 1281); the fibroblast-like cells derived from SV40-transformed African Green monkey kidney of the CV-1 lineage (ATCC CCL 70), of the COS-1 lineage (ATCC CRL 1650) and of the COS-7 lineage (ATCC CRL 1651); murine L-cells, murine 3T3 cells (ATCC CRL 1658), murine C127 cells, human embryonic kidney cells of the 293 lineage (ATCC CRL 1573), human carcinoma cells including those of the HeLa lineage (ATCC CCL 2), and neuroblastoma cells of the lines IMR-32 (ATCC CCL 127), SK-N-MC (ATCC HTB 10) and SK-N-SH (ATCC HTB 11).

A variety of gene expression systems have been adapted for use with those hosts and are now commercially available, and any one of these systems can be selected to drive expression of the EAA2 receptor-encoding DNA. These systems, available typically in the form of plasmidic vectors, incorporate expression cassettes the functional components of which include DNA constituting expression controlling sequences, which are host-recognized and enable expression of the receptor-encoding DNA when linked 5' thereof. The systems further incorporate DNA sequences which terminate expression when linked 3' of the receptor-encoding region. Thus, for expression in the selected mammalian cell host, there is generated a recombinant DNA expression construct in which DNA coding for the transportable receptor precursor is linked with expression controlling DNA sequences recognized by the host, and which include a region 5' of the receptor-encoding DNA to drive expression, and a 3' region to terminate expression. The plasmidic vector harbouring the expression construct typically incorporates such other functional components as an origin of replication, usually virally-derived, to permit replication of the plasmid in the expression host and desirably also for plasmid amplification in a bacterial host, such as *E. coli*. To provide a marker enabling selection of stably transformed recombinant cells, the vector will also incorporate a gene conferring some survival advantage on the transformants, such as a gene coding for neomycin resistance in which case the transformants are plated in medium supplemented with neomycin.

Included among the various recombinant DNA expression systems that can be used to achieve mammalian cell expression of the receptor-encoding DNA are those that exploit promoters of viruses that infect mammalian cells, such as the promoter from the cytomegalovirus (CMV), the Rous sarcoma virus (RSV), simian virus (SV40), murine mammary tumor virus (MMTV) and others. Also useful to drive expression are promoters such as the LTR of retroviruses, insect cell promoters such as those regulated by temperature, and isolated from Drosophila, as well as mammalian gene promoters such as those regulated by heavy metals, i.e., the metalothionein gene promoter, and other steroid-inducible promoters.

For incorporation into the recombinant DNA expression vector, DNA coding for the desired EAA2 receptor, i.e. the EAA2a receptor or a kainate-binding variant thereof, can be obtained by applying selected techniques of gene isolation or gene synthesis. As described in more detail in the examples herein, the EAA2a receptor, and the EAA2b and EAA2c variants thereof, are encoded within the genome of human brain tissue, and can therefore be obtained by careful application of conventional gene isolation and cloning techniques. This typically will entail extraction of total messenger RNA from a fresh source of human brain tissue, preferably cerebellum or hippocampus tissue, followed by conversion of message to cDNA and formation of a library in, for example, a bacterial plasmid, more typically a bacteriophage. Such bacteriophage harbouring fragments of the human DNA are typically grown by plating on a lawn of susceptible *E. coli* bacteria, such that individual phage plaques or colonies can be isolated. The DNA carried by the phage colony is then typically immobilized on a nitrocellulose or nylon-based hybridization membrane, and then hybridized, under carefully controlled conditions, to a radioactively (or otherwise) labelled oligonucleotide probe of appropriate sequence to identify the particular phage colony carrying receptor-encoding DNA or fragment thereof. Typically, the gene or a portion thereof so identified is subcloned into a plasmid vector for nucleic acid sequence analysis.

Having herein provided the nucleotide sequence of various human EAA2 receptors, it will be appreciated that automated techniques of gene synthesis and/or amplification can be performed to generate DNA coding therefor. Because of the length of the EAA2 receptor-encoding DNA, application of automated synthesis may require staged gene construction, in which regions of the gene up to about 300 nucleotides in length are synthesized individually and then ligated in correct succession for final assembly. Individually synthesized gene regions can be amplified prior to assembly, using polymerase chain reaction (PCR) technology.

The application of automated gene synthesis techniques provides an opportunity for generating sequence variants of naturally occurring members of the EAA2 gene family. It will be appreciated, for example, that polynucleotides coding for the EAA2 receptors herein described can be generated by substituting synonymous codons for those represented in the naturally occurring polynucleotide sequences herein identified. In addition, polynucleotides coding for synthetic variants of the EAA2 receptors herein described can be generated which, for example, incorporate one or more single amino acid substitutions, deletions or additions. Since it will for the most part be desirable to retain the natural ligand binding profile of the receptor for screening purposes, it is desirable to limit amino acid substitutions, for example to the so-called conservative replacements in which amino acids of like charge are substituted, and to limit substitutions to those sites less critical for receptor activity, e.g. within about the first 20 N-terminal residues of the mature receptor, and such other regions as are elucidated upon receptor domain mapping.

With appropriate template DNA in hand, the technique of PCR amplification may also be used to directly generate all or part of the final gene. In this case, primers are synthesized which will prime the PCR amplification of the final product, either in one piece, or in several pieces that may be ligated together. This may be via step-wise ligation of blunt ended, amplified DNA fragments, or preferentially via step-wise ligation of fragments containing naturally occurring restriction endonuclease sites. In this application, it is possible to use either cDNA or genomic DNA as the template for the PCR amplification. In the former case, the cDNA template can be obtained from commercially available or self-constructed cDNA libraries of various human brain tissues, including hippocampus and cerebellum.

Once obtained, the receptor-encoding DNA is incorporated for expression into any suitable expression vector, and host cells are transfected therewith using conventional procedures, such as DNA-mediated transformation, electroporation, or particle gun transformation. Expression vectors may be selected to provide transformed cell lines that express the receptor-encoding DNA either transiently or in a stable manner. For transient expression, host cells are typically transformed with an expression vector harbouring an origin of replication functional in a mammalian cell. For stable expression, such replication origins are unnecessary, but the vectors will typically harbour a gene coding for a product that confers on the transformants a survival advantage, to enable their selection. Genes coding for such selectable markers include the *E. coli* gpt gene which confers resistance to mycophenolic acid, the neogene from transposon Tn5 which confers resistance to the antibiotic G418 and to neomycin, the dhfr sequence from murine cells or *E. coli* which changes the phnotype of DHFR– cells into DHFR+ cells, and the tk gene of herpes simplex virus, which makes TK– cells phenotypically TK+ cells. Both transient expression and stable expression can provide transformed cell lines, and membrane preparations derived therefrom, for use in ligand screening assays.

For use in screening assays, cells transiently expressing the receptor-encoding DNA can be stored frozen for later use, but because the rapid rate of plasmid replication will lead ultimately to cell death, usually in a few days, the transformed cells should be used as soon as possible. Such assays may be performed either with intact cells, or with membrane preparations derived from such cells. The membrane preparations typically provide a more convenient substrate for the ligand binding experiments, and are therefore preferred as binding substrates. To prepare membrane preparations for screening purposes, i.e. ligand binding experiments, frozen intact cells are homogenized while in cold water suspension and a membrane pellet is collected after centrifugation. The pellet is then washed in cold water, and dialyzed to remove endogenous EAA ligands such as glutamate, that would otherwise compete for binding in the assays. The dialyzed membranes may then be used as such, or after storage in lyophilized form, in the ligand binding assays. Alternatively, intact, fresh cells harvested about two days after transient transfection or after about the same period following fresh plating of stably transfected cells can be used for ligand binding assays by the same methods as used for membrane preparations. When cells are used, the cells must be harvested by more gentle centrifugation so as not to damage them, and all washing must be done in a buffered medium, for example in phosphate-buffered saline, to avoid osmotic shock and rupture of the cells.

The binding of a candidate ligand to a selected human EAA2 receptor of the invention is evaluated typically using a predetermined amount of cell-derived membrane (measured, for example, by protein determination), generally from about 25 ug to 100 ug. Generally, competitive binding assays will be useful to evaluate the affinity of a test compound relative to kainate. This competitive binding assay can be performed by incubating the membrane preparation with radiolabelled kainate, for example (3H-kainate, in the presence of unlabelled test compound added at varying concentrations. Following incubations, either displaced or bound radiolabelled kainate can be recovered and measured to determine the relative binding affinities of the test compound and kainate for the particular receptor used as substrate. In this way, the affinities of various compounds for the kainate-type human EAA receptors can be measured.

As an alternative to using cells that express receptor-encoding DNA, ligand characterization may also be performed using cells, for example, *Xenopus oocytes,* that yield functional membrane-bound receptor following introduction of messenger RNA coding for the EAA2 receptor. In this case, the EAA2 receptor gene of the invention is typically subcloned into a plasmidic vector such that the introduced gene may be easily transcribed into RNA via an adjacent RNA transcription promoter supplied by the plasmidic vector, for example the T3 or T7 bacteriophage promoters. RNA is then transcribed from the inserted gene in vitro, and can then be injected into Xenopus oocytes. Following the injection of nL volumes of an RNA solution, the oocytes are left to incubate for up to several days, and are then tested for the ability to respond to a particular ligand molecule supplied in a bathing solution. Since functional EAA receptors act in part by operating a membrane channel through which ions may selectively pass, the functioning of the receptor in response to a particular ligand molecule in the bathing solution may typically be measured as an electrical current utilizing microelectrodes inserted into the cell.

In addition to using the receptor-encoding DNA to construct cell lines useful for ligand screening, expression of the DNA can, according to another aspect of the invention, be performed to produce fragments of the receptor in soluble form for structure investigation, to raise antibodies and for other experimental uses. It is expected that the portion of the EAA2 receptor responsible for binding a ligand molecule resides on the outside of the cell, i.e., is extracellular. It is therefore desirable in the first instance to facilitate the characterization of the receptor-ligand interaction by providing this extracellular ligand-binding domain in quantity and in isolated form, i.e., free from the remainder of the receptor. To accomplish this, the full-length EAA2 receptor-encoding DNA may be modified by site-directed mutagenesis, so as to introduce a translational stop condon into the extracellular N-terminal region, immediately before the sequence encoding the first transmembrane domain (TM1), i.e., before residue 528 as shown in FIG. 1. Since there will no longer be produced any transmembrane domain(s) to "anchor" the receptor into the membrane, expression of the modified gene will result in the secretion, in soluble form, of only the extracellular ligand-binding domain. Standard ligand-binding assays may then be performed to ascertain the degree of binding of a candidate compound to the extracellular domain so produced. It may of course be necessary, using site-directed mutagenesis, to produce several different versions of the extracellular regions, in order to optimize the degree of ligand binding to the isolated domains.

Alternatively, it may be desirable to produce an extracellular domain of the receptor which is not derived from the amino-terminus of the mature protein, but rather from the carboxyterminus instead, for example, domains immediately following the fourth transmembrane domain (TM4), i.e., residing between amino acid residues 806 and 962 of FIG. 1. In this case, site-directed mutagenesis and/or PCR-based amplification techniques may readily be used to provide a defined fragment of the gene encoding the receptor domain of interest. Such a DNA sequence may be used to direct the expression of the desired receptor fragment, either intracellularly or in secreted fashion, provided that the DNA encoding the gene fragment is inserted adjacent to a translation start codon provided by the expression vector, and that the required translation reading frame is carefully conserved.

It will be appreciated that the production of such extracellular ligand binding domains may be accomplished in a variety of host cells. Mammalian cells such as CHO cells may be used for this purpose, the expression typically being driven by an expression promotor capable of high-level expression, for example the CMV (cytomegalovirus) promotor. Alternatively, non-mammalian cells, such as insect Sf9 (Spodoptera frugiperda) cells may be used, with the expression typically being driven by expression promoters of the baculovirus, for example the strong, late polyhedrin protein promoter. Filamentous fungal expression systems may also be used to secrete large quantities of such extracellular domains of the EAA receptor. Aspergillus nidulans, for example, with the expression being driven by the alcA promotor, would constitute such an acceptable system. In addition to such expression hosts, it will be further appreciated that any prokaryotic or other eukaryotic expression system capable of expressing heterologous genes or gene fragments, whether intracellularly or extracellularly would be similarly acceptable.

The availability of isolated extracellular ligand-binding domains of the receptor protein makes it feasible to determine the 3-dimensional structures of these ligand-binding regions, with or without a candidate ligand complexed thereto, by a combination of X-ray crystallographic and advanced 2D-NMR techniques. In this way, additional new candidate compounds, predicted to have the required interactions with the 3-dimensional receptor structure, can be specifically designed and tested.

With large domains, crystallography is the method of choice for structure determination of both the domain in isolation, and of the co-complex with the natural ligand (or an appropriate antagonist or agonist molecule). If a particular domain can be made small enough, for example approximately 100–130 amino acids in length, then the powerful technique of 2-D NMR can also be applied to structure determination. This enables not only the determination of the domain structure, but also provides dynamic information about the drug-receptor interaction.

For use particularly in detecting the presence and/or location of an EAA2 receptor, for example in brain tissue, the present invention also provides, in another of its aspects, labelled antibody to a human EAA2 receptor. To raise such antibodies, there may be used as immunogen either the intact, soluble receptor or an immunogenic fragment thereof, produced in a microbial or mammalian cell host as described above or by standard peptide synthesis techniques. Regions of the EAA2a receptor particularly suitable for use as immunogenic fragments include those corresponding in sequence to an extracellular region of the receptor, or a portion of the extracellular region, such as peptides consisting of residues 1–527, including particularly residues 107–121 or 179–192 or 464–510, and peptides corresponding to regions between transmembrane domains Tm-2 and TM-3, such as a peptide consisting of residues 464–510. Peptides consisting of the C-terminal domain (residues 807–962) or a fragment thereof such as a peptide consisting of residues 927–942, may also be used for the raising of antibodies. Substantially the same regions of the human EAA2b and EAA2c receptors may also be used for production of antibodies against these receptors.

The raising of antibodies to the desired EAA2 receptor or immunogenic fragment can be achieved for polyclonal antibody production using immunization protocols of conventional design, and any of a variety of mammalian hosts, such as sheep, goats and rabbits. Alternatively, for monoclonal antibody production, immunocytes such as splenocytes can be received from the immunized animal and fused, using hybridoma technology, to a myeloma cells. The fusion products are then screened by culturing in a selection medium, and cells producing antibody are recovered for continuous growth and antibody recovery. Recovered antibody can then be coupled covalently to a detectable label, such as a radiolabel, enzyme label, luminescent label or the like, using linker technology established for this purpose.

In detectably labelled form, e.g. radiolabelled form, DNA or RNA coding for the human EAA2 receptor subunit, and selected regions thereof, may also be used, in accordance with another aspect of the present invention, as hybridization probes, for example, to identify sequence-related genes resident in the human or other mammalian genomes (or cDNA libraries) or to locate the EAA2-encoding DNA in a specimen, such as brain tissue. This can be done using either the intact coding region or a fragment thereof having radiolabelled, e.g., $^{32}P$, nucleotides incorporated therein. To identify the EAA2-encoding DNA in a specimen, it is desirable to use either the full length cDNA coding therefor, or a fragment which is unique thereto. With reference to FIG. 1 and the nucleotide numbering appearing thereon, such nucleotide fragments includes those corresponding in sequence to the following regions: 176–1580, 548–592, 1295–1376, 2844–2927, 3007–3120, 1856–1880, 1908–1929, 1998–2021, and 2298–2328. These sequences, and the intact gene itself, may also be used of course to clone EAA2-related genes by standard hybridization techniques.

EXAMPLE 1

Isolation of DNA coding for the human EAA2a receptor

As a first step in the isolation of DNA coding for a human EAA receptor, the published nucleotide sequences of rat GluR1 receptor and chicken and frog kainate binding proteins were compared to identify spaced regions of homology capable of serving as sites for primer binding and PCR-based amplification. Oligonucleotide primers putatively capable of hybridizing with sequence-related regions in human cDNA, and having non-hybridizing flanks bearing HindIII restriction sites for subsequent cloning work, were then synthesized based on the published sequence of the rat GluR1 gene using conventional techniques of gene synthesis, to generate primers of the following sequence:

5'GGGGTTTAAGCTTGAGCGTCGTCCTCT-TCCTGGT 3' (SEQ ID NO. 23)

5'GGGGTTTAAGCTTGTGAAGAACCACCA-GACGCCG 3' (SEQ ID NO. 24)

Using human hippocampal cDNA as template (obtained as an EcoRI-based lambda gt10 library from Clontech Laboratories, (Palo Alto, Calif., U.S.A.) the primers were then used in an attempt to amplify homologous sequences in the human cDNA, by application of the polymerase chain reaction technique. Reaction mixtures contained in 100 ul, 100 ng of human hippocampal cDNA, 125 pmol of each primer and 2U Taq polymerase (in 10 mM Tris-HCl, pH9.0, 50 mM KCl, 1.5 mM $MgCl_2$, and with 0.2 mM of each deoxyribonucleotide species). There were then performed thirty cycles of 94C/1 min; 58C/1 min; 72C/2 min, followed by a final cycle of 72C/30 min.

There was generated an amplification product having an expected nucleotide length (239 bp). The product of amplification was then liberated from the gel and subcloned for sequencing into the HindIII site of phagemid vector pTZ19 (Pharmacia). The nucleotide sequence of the amplification product (without primers) is represented, retrospectively, from nucleotide #1867 to nucleotide #2037 inclusive (FIG. 1). A comparison of the sequence amplified from the human cDNA template with the corresponding region of the rat GluR gene on which the oligonucleotide primers were based revealed only about 60% identity, indicating that a fragment from an unrelated human gene had been identified.

To isolate cDNA coding for the entire human EAA2a receptor, a lambda gt10-based library of human hippocampal cDNA was probed using a PCR-generated, labelled (alpha-$^{32}$P-dCTP) version of the 239 bp amplification product. Of $10^6$ clones screened, probing identified 60 putative clones under the following high stringency hybridization conditions: 6xSSC, 50% formamide, 5% Denhardt's solution, 0.5% SDS, 100 ug/ml denatured salmon sperm DNA. Hybridizations were carried out at 37C overnight, and filters were washed with 2xSSC containing 0.5% SDS at 25C for 5 minutes, followed by a 15 minute wash at 50C with 2xSSC containing 0.5% SDS. The final wash was with 1xSSC containing 0.5% SDS at 50C for 15 minutes. Filters were exposed to X-ray film (Kodak) overnight.

Hybridization studies were performed in duplicate, and only those clones which hybridized well in both duplicates were selected for further analysis. Upon second round screening, 50 of the original 60 putative clones were selected. All 50 putative clones were plaque-purified, large scale DNA preps were made, and then DNA inserts liberated therefrom were subcloned into the EcoRI site of pTZ18 vectors, for sequence analysis. Sequencing revealed one clone harbouring, internally, a region with a nucleotide sequence similar to the sequence of the original 239 bp subclone. The entire sequence of the isolated clone (442 bp) was then determined. Retrospectively, this 442 bp sub-clone is represented from nucleotide 1776 to nucleotide 2217 inclusive (FIG. 1).

Figure 3A:
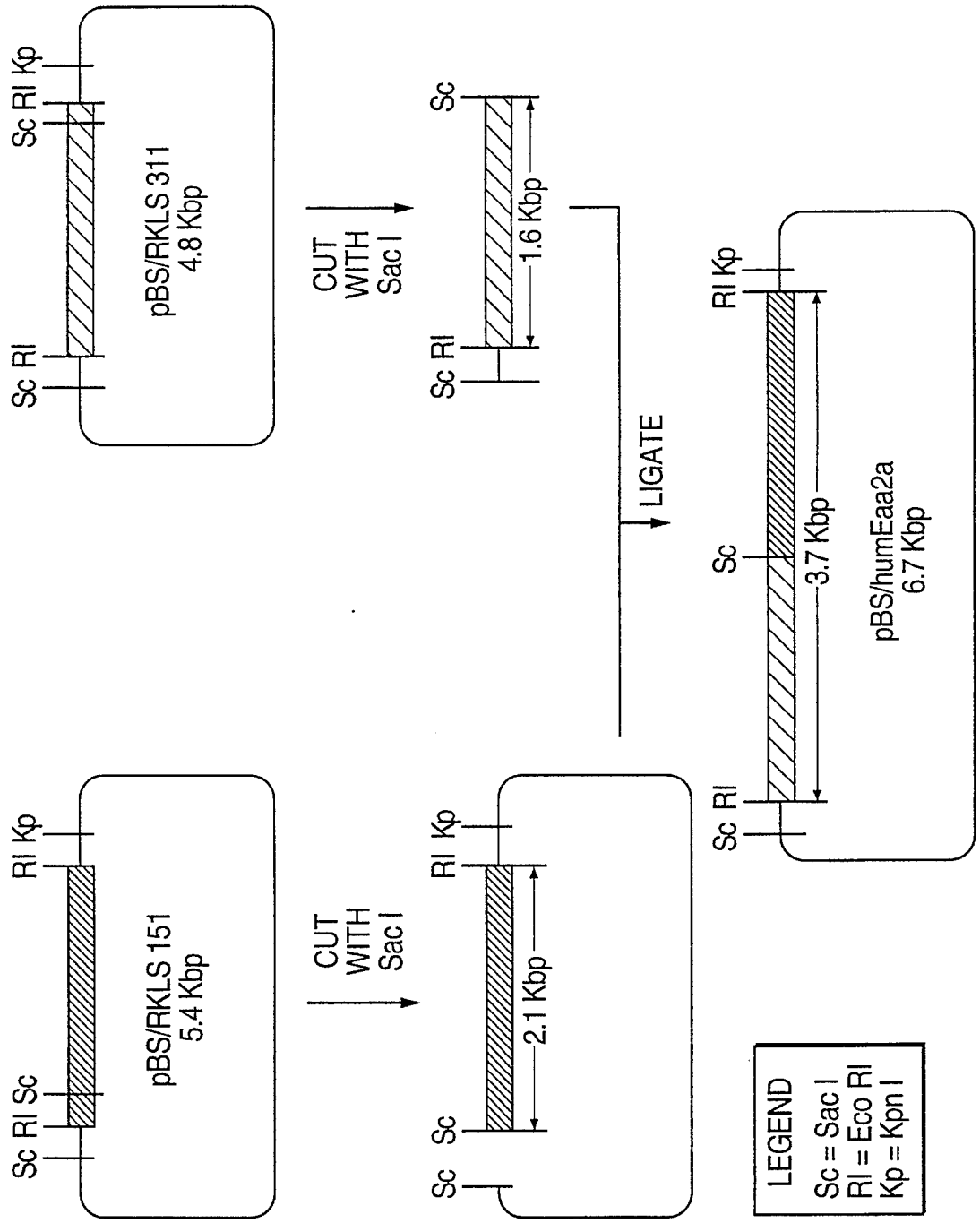
FIGS. 3(1) and 3(2) illustrate with linear plasmid maps the strategy used to construct expression vectors harbouring the DNA sequence illustrated in FIG. 1.
Figure 3B:
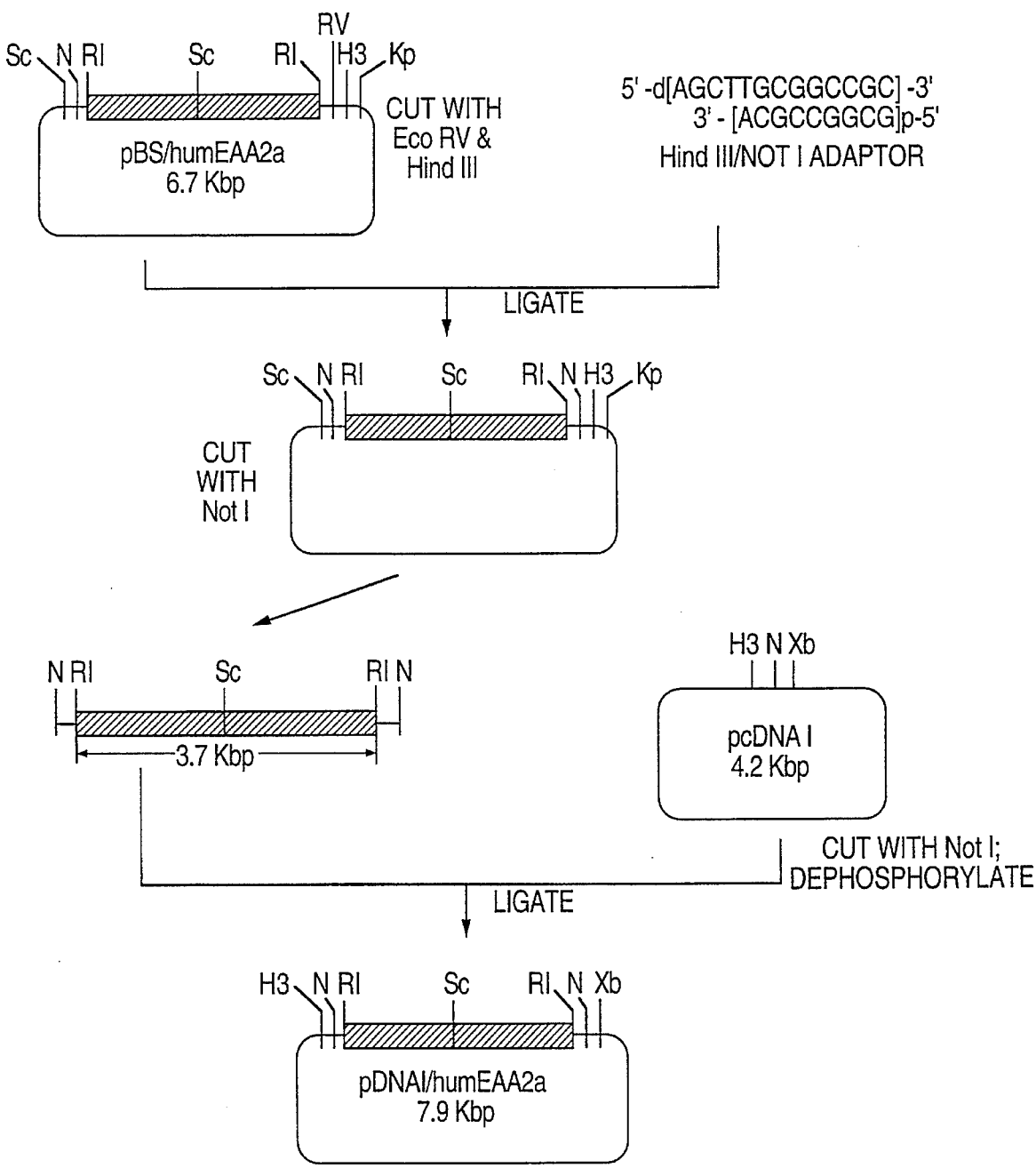

Since it was likely by analogy with the other receptor genes that the 442 bp was not full length, an alternative human hippocampal cDNA library constructed in a lambda phage system known commercially as lambda ZAP II was obtained (Stratagene Cloning Systems, La Jolla, Calif., U.S.A.) and screened using a PCR-generated, radiolabelled version of the 442 bp sub-clone. Screening of $10^6$ clones of this library by hybridization under the stringency conditions detailed above lead initially to the selection of 47 positive clones. For sequencing, phagemids carrying the inserts were excised, to generate insert-carrying variants of the phagemid vector known commercially as Bluescript-SK. Sequencing analysis identified two phagemid clones sharing a sequence overlap. One clone carrying a 1.Skb EcoRI/EcoRI insert, and apparently representing a 5' region of the open reading frame was designated pBS/RKLS311. The overlapping clone carrying a 2.4 kb EcoRI/EcoRI insert and appearing to represent the remaining 3' region of the open reading frame, was designated pBS/RKLS151. To construct the entire open reading frame, the strategy shown in FIG. 3 was employed to generate the phagemid pBS/HumEAA2a which carries the EAA2a-encoding DNA as a 3.7 kn EcoRI/EcoRI insert (recoverable intact as a 3.7 kb NotI/HindIII insert) in a 3.0 kb Bluescript-SK phagemid background. The entire sequence of the EcoRI insert is provided in FIG. 1.

The 6.7 kb phagemid pBS/humEAA2a was deposited, under the terms of the Budapest Treaty, with the American Type Culture Collection in Rockville, Md., U.S.A., on Aug. 21, 1991, and has been assigned accession number ATCC 75065.

EXAMPLE 2

Alternative strategy for obtaining EAA2a receptor-encoding DNA

Having herein provided the nucleotide sequence of EAA2a-encoding DNA, it will be appreciated that isolation thereof by the procedures just described is unnecessary, and can be replaced by application of automated techniques of gene synthesis and amplification. Using an appropriate cDNA library as template, for example a carefully prepared human hippocampal cDNA library, the polymerase chain reaction technique can be applied to amplify the desired cDNA product. While current PCR protocols are unlikely to enable direct amplification of the entire 3.7 kb gene, regional amplification to generate ligatable gene fragments is a feasible approach to gene construction.

Figure 2:
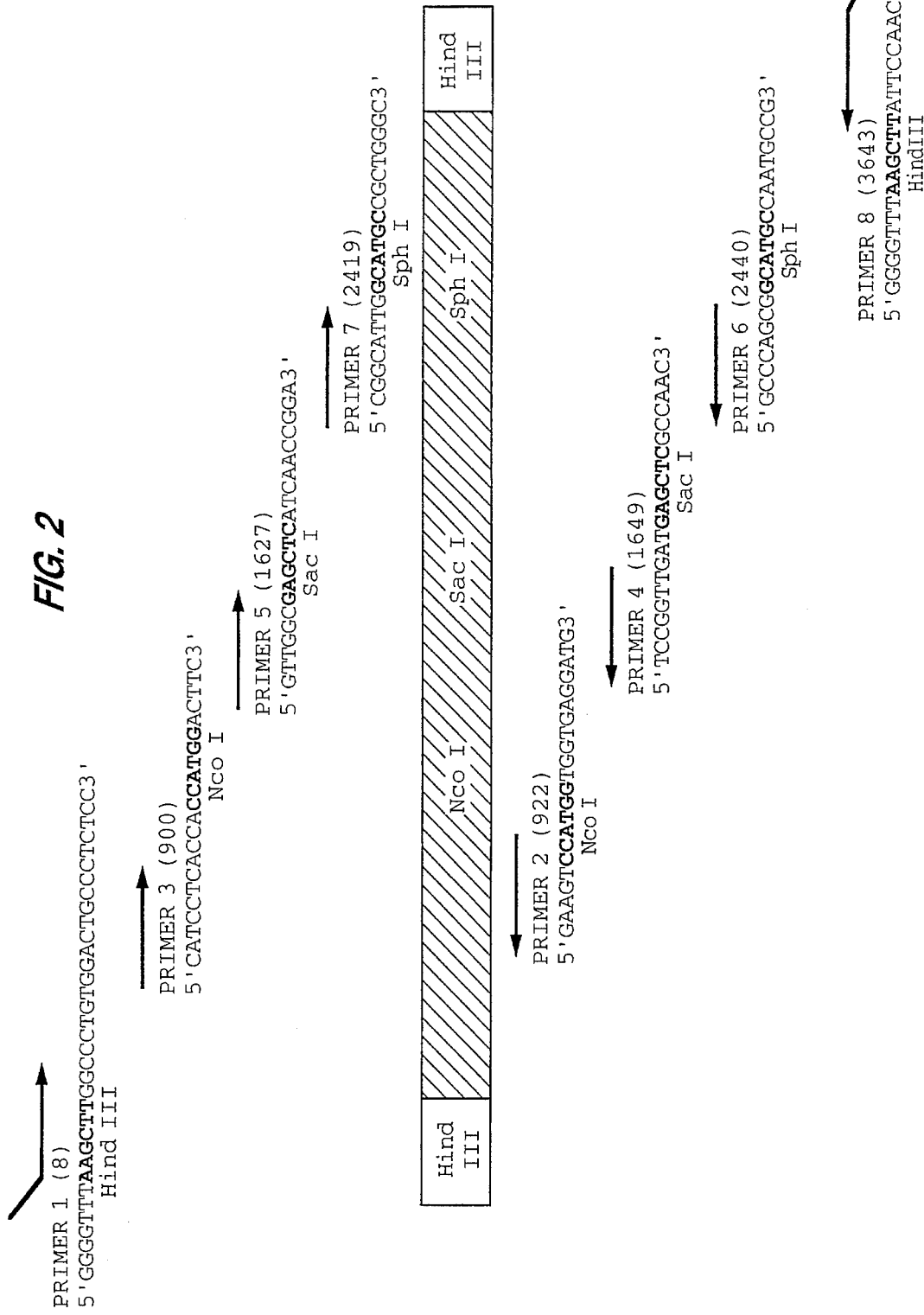
FIG. 2 illustrates schematically a PCR-based strategy for amplifying the DNA sequence illustrated in FIG. 1.

With reference specifically to the EAA2a-encoding DNA, PCR-facilitated gene construction can proceed, for example, as illustrated in FIG. 2. More particularly, regions of the cloned cDNA template are amplified as fragments comprising on the order of several hundred nucleotides using primers bearing non-hybridizing 5' flanks that constitute restriction sites useful in subsequent steps of gene assembly. In the example illustrated in FIG. 2, the gene is amplified as 4 individual fragments that can be ligated, because of the careful selection of restriction sites, in one step to form the entire EAA2a receptor-encoding DNA.

It will also be appreciated that automated techniques of gene synthesis can be applied to provide gene fragments that by PCR can be amplified and subsequently ligated. Using current protocols, for example, as described by Barnett et al., Nucl. Acids Res., 18(10):3094 (1990), fragments up to about 300 bases in length can be synthesized and then amplified again using restriction site-tailed primers to facilitate assembly of the de novo synthesized gene regions.

EXAMPLE 3

Construction of cell lines producing the human EAA2a receptor

For transient expression in mammalian cells, cDNA coding for the human EAA2a receptor was incorporated into the mammalian expression vector pcDNA1, which is available commercially from Invitrogen Corporation (San Diego, Calif., U.S.A.; catalogue number V490-20). This is a multifunctional 4.2 kb plasmid vector designed for cDNA expression in eukaryotic systems, and cDNA analysis in prokaryotes. Incorporated on the vector are the CMV promoter and enhancer, splice segment and polyadenylation signal, an SV40 and Polyoma virus origin of replication, and M13 origin to rescue single strand DNA for sequencing and mutagenesis, Sp6 and T7 RNA promoters for the production of sense and anti-sense and anti-sense RNA transcripts and a Col E1-like high copy plasmid origin. A polylinker is located appropriately downstream of the CMV promoter (and 3' of the T7 promoter).

For incorporation of the EAA2a receptor-encoding cDNA into an expression vector, the cDNA source phagemid pBS/humEAA2a was first modified to provide a NotI site 3' of the cDNA insert. This was achieved by restricting the phagemid, with HindIII and EcoRV, and then inserting a HindIII/NotI adaptor sequence in the HindIII site followed by blunt end ligation to recircularize the phagemid, to yield pBS/humEAA2a-NotI. This modification permitted the full length cDNA insert to be released as a 3.7 kb NotI/NotI fragment, which was then incorporated at the NotI site in the pcDNAI polylinker. Sequencing across the NotI junction was performed to confirm proper insert orientation in pcDNAI. The resulting plasmid, designated pcDNA1/humEAA2a, was then introduced for transient expression into a selected mammalian cell host, in this case the monkey-derived, fibroblast like cells of the COS-1 lineage (available from the American Type Culture Collection, Rockville, Md. as ATCC CRL 1650).

For transient expression of the EAA2-encoding DNA, COS-1 cells were transfected with approximately 8 ug DNA (as pcDNA1/humEAA2a) per $10^6$ COS cells, by DEAE-mediated DNA transfection and treated with chloroquine according to the procedures described by Maniatis et al, supra. Briefly, COS-1 cells were plated at a density of $5\times10^6$ cells/dish and then grown for 24 hours in FBS-supplemented DMEM-F12 medium. Medium was then removed and cells were washed in PBS and then in medium. There was then applied on the cells 10 ml of a transfection solution containing DEAE dextran (0.4 mg/ml), 100 uM chloroquine, 10% NuSerum, DNA (0.4 mg/ml) in DMEM/F12 medium. After incubation for 3 hours at 37C, dells were washed in PBS and medium as just described and then shocked for 1 minute with 10% DMSO in DMEM/F12 medium. Cells were allowed to grow for 2–3 days in 10% FBS-supplemented medium, and at the end of incubation dishes were placed on ice, washed with ice cold PBS and then removed by scraping. Cells were then harvested by centrifugation at 1000 rpm for 10 minutes and the cellular pellet was frozen in liquid nitrogen, for subsequent use in ligand binding assays. Northern blot analysis of a thawed aliquot of frozen cells confirmed expression of receptor-encoding cDNA in cells under storage.

In a like manner, stably transfected cell lines were also prepared using two different cell types as host: CHO K1 and CHO Pro5. To construct these cell lines, cDNA coding for human EAA2a was incorporated into the NotI site of a 7.1kb derivative of plasmid vector pcDNA1, which incorporates the neomycin gene under control of the Rous Sarcoma Virus LTR promoter and is designed pcDNA1/NEO (available also from Invitrogen Corporation, catalogue XV492-20). In a similar fashion, and again using a convenient NotI site for insertion, the receptor-encoding cDNA was inserted into the mammalian expression vector pRC/CMV (Invitrogen), which enables stable expression. Insertion at this site placed the cDNA under the expression control of the cytomegalovirus promoter and upstream of the polyadenylation site and terminator of the bovine growth hormone gene, and into a vector background comprising the neomycin resistance gene (driven by the SV40 early promoter) as selectable marker.

To introduce plasmids constructed as described above, the host CHO cells were first seeded at a density of $5\times10^5$ in 10% FBS-supplemented MEM medium. After growth for 24 hours, fresh medium was added to the plates and three hours later the cells were transfected using the calcium phosphate-DNA co-precipitation procedure (Maniatis et al, supra). Briefly, 3 ug of DNA was mixed and incubated with buffered calcium solution for 10 minutes at room temperature. An equal volume of buffered phosphate solution was added and the suspension was incubated for 15 minutes at room temperature. Next, the incubated suspension was applied to the cells for 4 hours, removed, and the cells were shocked with medium containing 15% glycerol. Three minutes later, cells were washed with medium and incubated for 24 hours at normal growth conditions. Cells resistant to neomycin were selected in 10% FBS-supplemented alpha-MEM medium containing G418 (1 mg/ml). Individual colonies of G418-resistant cells were isolated about 2–3 weeks later, clonally selected, and then propagated for assay purposes.

EXAMPLE 4

Ligand Binding assays

Transfected cells in the frozen state were resuspended in ice-cold distilled water using a hand homogenizer and centrifuged for 20 minutes at 50,000 g. The supernatant was discarded and the membrane pellet stored frozen at −70C.

COS cell membrane pellets were suspended in ice cold 50 mMTris-HCl (pH 7.55, 5C) and placed inside Spectrapor 7 (EDTA-treated, sulfur-free) dialysis tubing. The suspension was placed in 4 liters of ice cold 50 mM Tris-HCl (pH 7.55, 5C) and dialyzed for 16–24 hours at 5C in order to remove endogenous glutamate that would compete for binding. The tissue suspension was recovered from the tubing along with a small volume of buffer used to rinse the tubing. This resultant membrane preparation was used as tissue source for binding experiments described below. Proteins were determined using the Pierce Reagent with BSA as standard.

Binding assays were then performed, using an amount of COS-delivered membrane equivalent to from 25–100 ug as judged by protein determination and selected radiolabelled ligand. In particular, glutamate binding assays entailed formation of an incubation mixture consisting of 25–100 ug of tissue protein, and [3,4-3H]L-glutamic acid (47.3 Ci/mmole, 10 nM final) in 50 mM Tris-HCl (pH 7.55, 5C) in 1 ml final volume. Non-specific binding was in the presence of 1 mML-glutamate. Samples were incubated on ice for 60 minutes in plastic minivials. Bound and free ligand were separated by centrifugation for 10 minutes at 50,000 g (4C). Tissue pellets were washed superficially with 2×6 ml of ice cold incubation buffer. Pellets were solubilized and counted in 5 ml of Beckman Ready Protein Scintillation cocktail.

For kainate binding assays, incubation mixtures consisted of 25–100 ug tissue protein and [vinylidene-3H] kainic acid (58 Ci/mmole, 5 nM final) in the cold incubation buffer, 1 ml final volume. Non-specific binding was in the presence of 1 mM L-glutamate. Samples were incubated as for the glutamate binding assays, and bound and free ligand were separated by rapid filtration using a Brandel cell harvester and GF/B filters presoaked in ice-cold 0.3% polyethyleneimine. Filters were washed twice in 6 ml of the cold incubation buffer, then placed in scintillation vials with 5 ml of Beckman Ready-Safe scintillation cocktail for counting.

AMPA-binding assays were also performed in substantially the same manner described above for kainate binding, but using as ligand D,L-alpha[5-methyl-3H]amino- 3-hydroxy-5-methylisoxazole-4-propionic acid (3H-AMPA, 27.6 Ci/mmole, 5 nM final) with 0.1M KSCN and 2.5 mM caCl$_2$ in the 1 ml final volume.

Figure 5A:
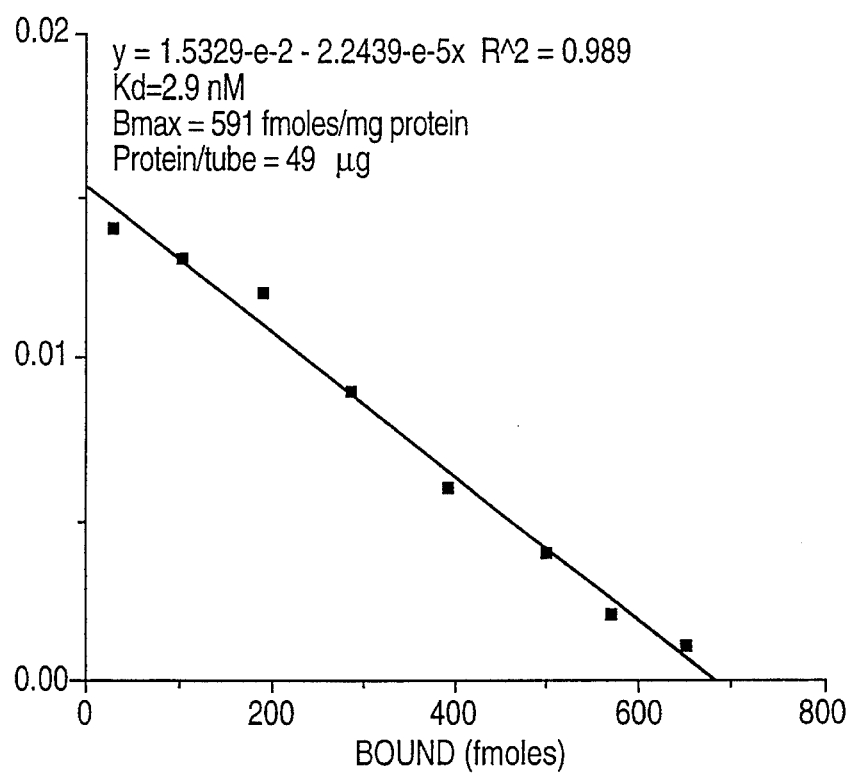
Figure 5B:
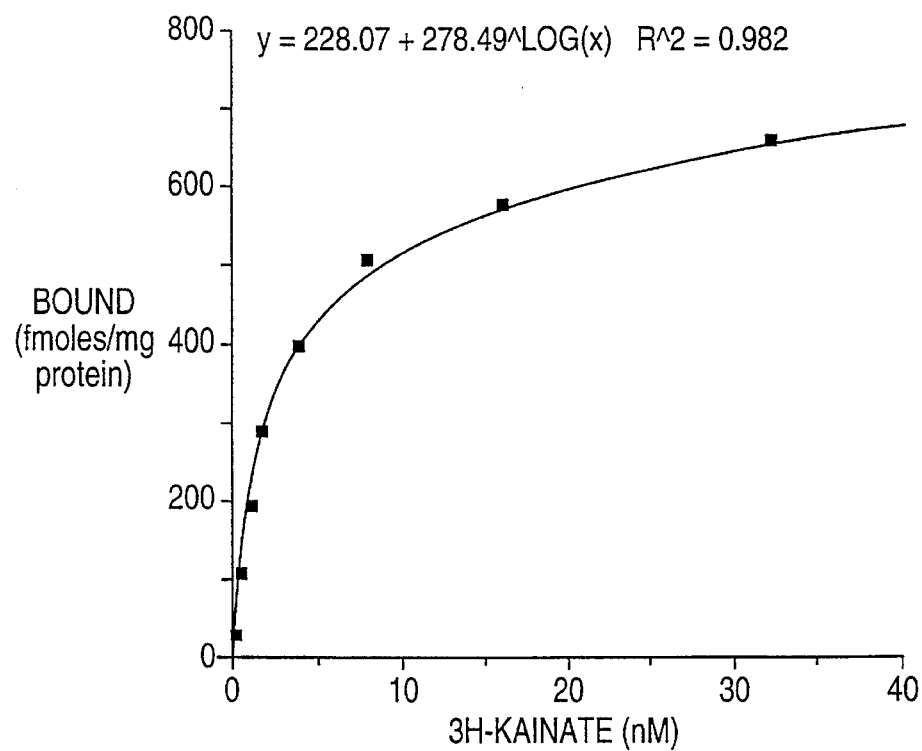

Assays performed in this manner revealed specific [3H]-kainate binding at 5 nM and [3H]-glutamate binding at 10 nM, labelled ligand. Scatchard analysis indicated that the recombinantly expressed human EAA2a receptor contained a single class of [3H]-labelled kainate binding sites with a dissocation constant (Kd) of 2.9 nM (FIG. 5), and a maximum binding (Bmax) of 691 fmol/mg protein. Mock transfected cells exhibited no specific binding of any of the ligands tested.

Additional assays were also performed, the results of which are shown in FIG. 6. Displacement of [3H]-labelled kainate binding with the noted selective ligands showed a rank order of potency of: kainate>domoate>quisqualate>glutamate>DNQX>dihydrokainate>CNQX>AMPA. No displacement of kainate was observed with NMDA or 1S,3R-ACPD at concentrations up to 100 uM.

The data obtained with the ligand-binding assays demonstrate clearly that the EAA2a receptor is binding kainate with high affinity. This activity, coupled with the fact that there is little or no demonstrable binding of either AMPA or NMDA clearly assigns the EAA2a receptor to be of the kainate type of EAA receptor. Furthermore, this binding profile, especially with the kainate binding being of the high affinity category (i.e. nanomolar range) indicates that the receptor is functioning in an authentic manner, and can therefore reliably predict the ligand binding "signature" of its non-recombinant counterpart from the intact human brain. These features make the recombinant receptor especially useful for selecting and characterizing ligand compounds which bind to the receptor, and/or for selecting and characterizing compounds which may act by displacing other ligands from the receptor. The isolation of the EAA2a receptor gene in a pure form, capable of being expressed as a single, homogenous receptor species, therefore frees the ligand binding assay from the lack of precision introduced when complex, heterogeneous receptor preparations from human brains are used to attempt such characterizations.

EXAMPLE 5

Naturally occurring variants of the human EAA2a receptor

Using the same 442 bp probe which lead to the successful identification of the human EAA2a receptor, two sequence-related variants thereof were also identified and isolated, in substantially the same manner. As shown in FIG. 4, one variant designated EAA2b is nearly identical in all structural respects to the human EAA2a receptor, and differs only by the precise insertion in EAA2b of the glutamine-encoding triplet CAG between nucleotide positions 1648 and 1649 of EAA2a. Like DNA coding for EAA2a, the EAA2b-encoding DNA was isolated from a cDNA library of human hippocampal DNA. To construct the full length cDNA containing the entire open reading frame, overlapping clones pBSRKLS311 (representing the 5'-region) and pBS/RKLS511 (representing the 3'-region) were used in the same manner as described for humEAA2a. For binding studies, the isolated cDNA was tailored first to incorporate the 3' NotI site, and was then introduced for transient expression into cells of the COS-1 lineage after insertion into the vector pcDNA1 (transient expression) and into CHO K1 or CHO Pro5 cell after insertion into vectors pcDNA1/NEO or pRC/CMV all in the same manner was described above for human EAA2a. Ligand binding studies, while preliminary, indicate the same pattern of ligand binding affinity, and thus demonstrate that the EAA2b variant is also a human EAA receptor of the kainate-binding-type.

A plasmid, designated pBS/humEAA2b, which carries a 3.7 kb NotIHindIII cDNA insert coding for the human EAA2b receptor in a 3.0 kb Bluescript-SK background, has been deposited, under the terms of the Budapest Treaty, with the American Type Culture Collection in Rockville, Md. U.S.A. on Aug. 21, 1991, under accession number ATCC 75066.

Isolation of two additional EAA2a variants, designated EAA2c and EAA2d, has demonstrated that expression of genes coding for human EAA receptors of the kainate type is not restricted to hippocampal tissue. More particularly, whereas both human EAA2a and human EAA2b were isolated after probing hippocampal cDNA libraries, the variant EAA2c was isolated using the same 442 bp probe from a library of human cerebellum cDNA, (available from Stratagene Cloning Systems). The variant EAA2d, on the other hand, was isolated similarly but from a human fetal brain cDNA library. While sequencing of a minor 5' portion of the EAA2c and EAA2d coding regions remains to be completed, it is clear, as shown in FIG. 4, that both EAA2c and EAA2d differ from EAA2a in a short region representing the signal peptide and at the extracellular N-terminus of the mature protein.

What is claimed is:

1. A method of assaying a candidate ligand compound for binding affinity to a human EAA receptor, which comprises the steps of incubating a labeled form of said compound with a cell or with a membrane preparation derived from said cell, said cell having incorporated expressibly therein a heterologous DNA molecule that encodes a human EAA2 receptor, having the amino acid sequence of residues 1–962 of SEQ ID NO:2, or a kainate-binding variant of said EAA2 receptor which is at least 95% homologous to said EAA2 receptor, washing unbound ligand compound from the incubation mixture, and then determining the presence of membrane-bound ligand compound.

2. A method for determining the binding affinity of a candidate ligand compound for a human EAA receptor, which comprises the steps of incubating a cell or a membrane preparation derived from said cell with a labeled EAA receptor ligand to form a ligand/receptor complex, said cell having incorporated expressibly therein a heterologous DNA molecule that encodes a human EAA2 receptor having the amino acid sequence of residues 1–962 of SEQ ID NO:2 or a kainate-binding variant of said EAA2 receptor which is at least 95% homologous to said EAA2 receptor, removing unbound ligand, incubating the receptor/ligand complex with said compound, and measuring the amount of labeled ligand displaced from or remaining in the receptor/ligand complex.

* * * * *

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 3695 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: sig_peptide
        ( B ) LOCATION: 176..229

(ix) FEATURE:
    (A) NAME/KEY: mat_peptide
    (B) LOCATION: 230..3118

(ix) FEATURE:
    (A) NAME/KEY: CDS
    (B) LOCATION: 176..3118

(xi) SEQUENCE DESCRIPTION: SEQ ID NO:1:

```
GAATTCCGGC CCTGTGGACT GCCCTCTCCC CCCGCCCAGC CCCACCACCA CCCAGCGCCA      60

GAGCCACCTC CCGCTGTCGG TCTGCGGGCC TCGAGGGAGC CCAGCCCTCC GTCCCACCAG     120

GATCCGTGGC GAGTGGGGGC CGCGGCAGCT GCGTCCCCAT GAGGAGGGGA GGAAG ATG     178
                                                              Met
                                                              -18

CCG GCT GAG CTG CTG CTG CTG CTG ATT GTT GCC TTC GCC AGC CCC AGC      226
Pro Ala Glu Leu Leu Leu Leu Leu Ile Val Ala Phe Ala Ser Pro Ser
        -15                 -10                  -5

TGC CAG GTG CTC TCA TCA CTG CGC ATG GCT GCA ATC CTG GAT GAT CAG      274
Cys Gln Val Leu Ser Ser Leu Arg Met Ala Ala Ile Leu Asp Asp Gln
  1              5                 10                     15

ACA GTG TGT GGC CGC GGT GAG CGT CTG GCC TTG GCC TTG GCC CGG GAG      322
Thr Val Cys Gly Arg Gly Glu Arg Leu Ala Leu Ala Leu Ala Arg Glu
             20                 25                 30

CAG ATC AAC GGG ATC ATC GAG GTC CCA GCC AAG GCC CGA GTG GAA GTA      370
Gln Ile Asn Gly Ile Ile Glu Val Pro Ala Lys Ala Arg Val Glu Val
                35                 40                 45

GAC ATC TTT GAG CTG CAG CGG GAC AGC CAG TAC GAG ACC ACG GAC ACC      418
Asp Ile Phe Glu Leu Gln Arg Asp Ser Gln Tyr Glu Thr Thr Asp Thr
            50                 55                 60

ATG TGT CAG ATC TTA CCC AAA GGG GTT GTG TCT GTC CTT GGG CCC TCC      466
Met Cys Gln Ile Leu Pro Lys Gly Val Val Ser Val Leu Gly Pro Ser
     65                 70                 75

TCT AGC CCA GCA TCT GCC TCC ACC GTG AGC CAT ATC TGT GGA GAG AAG      514
Ser Ser Pro Ala Ser Ala Ser Thr Val Ser His Ile Cys Gly Glu Lys
 80                 85                 90                 95

GAG ATC CCC CAC ATC AAG GTG GGT CCC GAG GAG ACA CCC CGC CTT CAG      562
Glu Ile Pro His Ile Lys Val Gly Pro Glu Glu Thr Pro Arg Leu Gln
                100                105                110

TAC CTT CGC TTC GCG TCT GTC AGC CTG TAC CCC AGT AAC GAG GAC GTC      610
Tyr Leu Arg Phe Ala Ser Val Ser Leu Tyr Pro Ser Asn Glu Asp Val
            115                120                125

AGC TTG GCG GTC TCC CGA ATC CTC AAG TCC TTC AAC TAC CCC TCG GCC      658
Ser Leu Ala Val Ser Arg Ile Leu Lys Ser Phe Asn Tyr Pro Ser Ala
        130                135                140

AGC CTC ATC TGC GCC AAG GCT GAG TGC CTG CTG CGA TTG GAG GAA CTG      706
Ser Leu Ile Cys Ala Lys Ala Glu Cys Leu Leu Arg Leu Glu Glu Leu
145                150                155

GTG CGT GGC TTC CTC ATC TCC AAG GAG ACG CTG TCA GTG AGG ATG TTG      754
Val Arg Gly Phe Leu Ile Ser Lys Glu Thr Leu Ser Val Arg Met Leu
160                165                170                175

GAC GAC AGC CGG GAC CCC ACA CCA CTG CTC AAG GAG ATC CGT GAT GAC      802
Asp Asp Ser Arg Asp Pro Thr Pro Leu Leu Lys Glu Ile Arg Asp Asp
            180                185                190

AAG GTG TCC ACC ATC ATC ATC GAC GCC AAC GCC TCC ATC TCC CAC CTC      850
Lys Val Ser Thr Ile Ile Ile Asp Ala Asn Ala Ser Ile Ser His Leu
        195                200                205

ATC CTC CGT AAG GCC TCG GAA CTG GGA ATG ACC TCA GCG TTT TAC AAG      898
Ile Leu Arg Lys Ala Ser Glu Leu Gly Met Thr Ser Ala Phe Tyr Lys
    210                215                220

TAC ATC CTC ACC ACC ATG GAC TTC CCC ATC CTG CAT CTG GAC GGT ATT      946
```

| | | | | | | | | | | | | | | |
|---|---|---|---|---|---|---|---|---|---|---|---|---|---|---|
|Tyr|Ile|Leu|Thr|Thr|Met|Asp|Phe|Pro|Ile|Leu|His|Leu|Asp|Gly|Ile|
| |225| | | |230| | | | | |235| | | | |

| | | | | | | | | | | | | | | | | |
|---|---|---|---|---|---|---|---|---|---|---|---|---|---|---|---|---|
|GTG|GAG|GAC|TCC|TCC|AAC|ATC|CTG|GGC|TTC|TCC|ATG|TTC|AAC|ACG|TCC|994|
|Val|Glu|Asp|Ser|Ser|Asn|Ile|Leu|Gly|Phe|Ser|Met|Phe|Asn|Thr|Ser| |
|240| | | | |245| | | | |250| | | | |255| |

|CAC|CCC|TTC|TAC|CCT|GAG|TTT|GTC|CGC|AGC|CTC|AAC|ATG|TCC|TGG|AGG|1042|
|---|---|---|---|---|---|---|---|---|---|---|---|---|---|---|---|---|
|His|Pro|Phe|Tyr|Pro|Glu|Phe|Val|Arg|Ser|Leu|Asn|Met|Ser|Trp|Arg| |
| | | | |260| | | | |265| | | | |270| | |

|GAG|AAC|TGT|GAA|GCC|AGC|ACC|TAC|CTG|GGC|CCT|GCG|CTG|TCA|GCC|GCC|1090|
|---|---|---|---|---|---|---|---|---|---|---|---|---|---|---|---|---|
|Glu|Asn|Cys|Glu|Ala|Ser|Thr|Tyr|Leu|Gly|Pro|Ala|Leu|Ser|Ala|Ala| |
| | |275| | | | |280| | | | |285| | | | |

|CTG|ATG|TTT|GAC|GCC|GTG|CAC|GTG|GTG|GTG|AGC|GCT|GTC|CGA|GAG|CTG|1138|
|---|---|---|---|---|---|---|---|---|---|---|---|---|---|---|---|---|
|Leu|Met|Phe|Asp|Ala|Val|His|Val|Val|Val|Ser|Ala|Val|Arg|Glu|Leu| |
| | |290| | | | |295| | | | |300| | | | |

|AAC|CGC|AGC|CAG|GAG|ATC|GGT|GTG|AAG|CCT|CTG|GCC|TGT|ACA|TCG|GCC|1186|
|---|---|---|---|---|---|---|---|---|---|---|---|---|---|---|---|---|
|Asn|Arg|Ser|Gln|Glu|Ile|Gly|Val|Lys|Pro|Leu|Ala|Cys|Thr|Ser|Ala| |
| |305| | | | |310| | | | |315| | | | | |

|AAC|ATT|TGG|CCC|CAC|GGG|ACC|AGC|CTC|ATG|AAC|TAC|CTG|CGC|ATG|GTA|1234|
|---|---|---|---|---|---|---|---|---|---|---|---|---|---|---|---|---|
|Asn|Ile|Trp|Pro|His|Gly|Thr|Ser|Leu|Met|Asn|Tyr|Leu|Arg|Met|Val| |
|320| | | | |325| | | | |330| | | | |335| |

|GAG|TAT|GAT|GGG|CTG|ACC|GGG|CGG|GTC|GAG|TTC|AAC|AGC|AAA|GGG|CAG|1282|
|---|---|---|---|---|---|---|---|---|---|---|---|---|---|---|---|---|
|Glu|Tyr|Asp|Gly|Leu|Thr|Gly|Arg|Val|Glu|Phe|Asn|Ser|Lys|Gly|Gln| |
| | | | |340| | | | |345| | | | |350| | |

|AGA|ACC|AAC|TAC|ACC|CTG|CGC|ATC|CTA|GAA|AAG|TCC|CGG|CAG|GGC|CAC|1330|
|---|---|---|---|---|---|---|---|---|---|---|---|---|---|---|---|---|
|Arg|Thr|Asn|Tyr|Thr|Leu|Arg|Ile|Leu|Glu|Lys|Ser|Arg|Gln|Gly|His| |
| | | |355| | | | |360| | | | |365| | | |

|CGT|GAG|ATT|GGG|GTG|TGG|TAC|TCT|AAC|CGC|ACC|CTG|GCC|ATG|AAT|GCC|1378|
|---|---|---|---|---|---|---|---|---|---|---|---|---|---|---|---|---|
|Arg|Glu|Ile|Gly|Val|Trp|Tyr|Ser|Asn|Arg|Thr|Leu|Ala|Met|Asn|Ala| |
| | |370| | | | |375| | | | |380| | | | |

|ACC|ACC|CTG|GAC|ATC|AAC|CTG|TCG|CAG|ACA|CTG|GCC|AAC|AAG|ACC|CTG|1426|
|---|---|---|---|---|---|---|---|---|---|---|---|---|---|---|---|---|
|Thr|Thr|Leu|Asp|Ile|Asn|Leu|Ser|Gln|Thr|Leu|Ala|Asn|Lys|Thr|Leu| |
| |385| | | | |390| | | | |395| | | | | |

|GTG|GTC|ACA|ACC|ATC|CTG|GAG|AAC|CCA|TAC|GTC|ATG|CGC|CGG|CCC|AAC|1474|
|---|---|---|---|---|---|---|---|---|---|---|---|---|---|---|---|---|
|Val|Val|Thr|Thr|Ile|Leu|Glu|Asn|Pro|Tyr|Val|Met|Arg|Arg|Pro|Asn| |
|400| | | | |405| | | | |410| | | | |415| |

|TTC|CAG|GGC|CTG|TCG|GGG|AAC|GAA|CGC|TTC|GAG|GGC|TTC|TGC|GTG|GAC|1522|
|---|---|---|---|---|---|---|---|---|---|---|---|---|---|---|---|---|
|Phe|Gln|Gly|Leu|Ser|Gly|Asn|Glu|Arg|Phe|Glu|Gly|Phe|Cys|Val|Asp| |
| | | | |420| | | | |425| | | | |430| | |

|ATG|CTG|CGG|GAG|CTG|GCC|GAG|CTG|CTG|CCG|TTC|CCG|TAC|CGC|CTG|CGG|1570|
|---|---|---|---|---|---|---|---|---|---|---|---|---|---|---|---|---|
|Met|Leu|Arg|Glu|Leu|Ala|Glu|Leu|Leu|Pro|Phe|Pro|Tyr|Arg|Leu|Arg| |
| | | |435| | | | |440| | | | |445| | | |

|TTG|GTG|GAG|GAT|GGG|CTG|TAC|GGG|GCG|CCC|GAG|CCC|AAC|GGC|TCC|TGG|1618|
|---|---|---|---|---|---|---|---|---|---|---|---|---|---|---|---|---|
|Leu|Val|Glu|Asp|Gly|Leu|Tyr|Gly|Ala|Pro|Glu|Pro|Asn|Gly|Ser|Trp| |
| | |450| | | | |455| | | | |460| | | | |

|ACG|GGC|ATG|GTT|GGC|GAG|CTC|ATC|AAC|CGG|AAG|GCA|GAC|CTG|GCT|GTG|1666|
|---|---|---|---|---|---|---|---|---|---|---|---|---|---|---|---|---|
|Thr|Gly|Met|Val|Gly|Glu|Leu|Ile|Asn|Arg|Lys|Ala|Asp|Leu|Ala|Val| |
| |465| | | | |470| | | | |475| | | | | |

|GCC|GCC|TTC|ACC|ATC|ACA|GCT|GAG|CGG|GAG|AAG|GTC|ATC|GAC|TTT|TCC|1714|
|---|---|---|---|---|---|---|---|---|---|---|---|---|---|---|---|---|
|Ala|Ala|Phe|Thr|Ile|Thr|Ala|Glu|Arg|Glu|Lys|Val|Ile|Asp|Phe|Ser| |
|480| | | | |485| | | | |490| | | | |495| |

|AAG|CCC|TTT|ATG|ACC|CTG|GGG|ATC|AGC|ATC|CTC|TAC|CGA|GTG|CAC|ATG|1762|
|---|---|---|---|---|---|---|---|---|---|---|---|---|---|---|---|---|
|Lys|Pro|Phe|Met|Thr|Leu|Gly|Ile|Ser|Ile|Leu|Tyr|Arg|Val|His|Met| |
| | | | |500| | | | |505| | | | |510| | |

|GGC|CGC|AAG|CCT|GGC|TAC|TTC|TCC|TTC|CTG|GAC|CCC|TTC|TCC|CCT|GCT|1810|
|---|---|---|---|---|---|---|---|---|---|---|---|---|---|---|---|---|
|Gly|Arg|Lys|Pro|Gly|Tyr|Phe|Ser|Phe|Leu|Asp|Pro|Phe|Ser|Pro|Ala| |
| | | |515| | | | |520| | | | |525| | | |

|GTG|TGG|CTC|TTC|ATG|CTT|CTT|GCC|TAC|CTG|GCT|GTC|AGC|TGC|GTC|CTG|1858|
|---|---|---|---|---|---|---|---|---|---|---|---|---|---|---|---|---|
|Val|Trp|Leu|Phe|Met|Leu|Leu|Ala|Tyr|Leu|Ala|Val|Ser|Cys|Val|Leu| |
| | |530| | | | |535| | | | |540| | | | |

|TTT|CTG|GCT|GCC|AGG|CTG|AGC|CCC|TAT|GAG|TGG|TAT|AAC|CCA|CAC|CCA|1906|
|---|---|---|---|---|---|---|---|---|---|---|---|---|---|---|---|---|

```
                Phe  Leu  Ala  Ala  Arg  Leu  Ser  Pro  Tyr  Glu  Trp  Tyr  Asn  Pro  His  Pro
                     545                      550                      555

TGC  CTG  CGG  GCA  CGC  CCC  CAC  ATC  CTG  GAG  AAC  CAG  TAC  ACG  CTG  GGC                    1954
Cys  Leu  Arg  Ala  Arg  Pro  His  Ile  Leu  Glu  Asn  Gln  Tyr  Thr  Leu  Gly
560                      565                      570                      575

AAC  AGC  CTG  TGG  TTT  CCC  GTG  GGG  GGC  TTC  ATG  CAG  CAG  GGC  TCG  GAG                    2002
Asn  Ser  Leu  Trp  Phe  Pro  Val  Gly  Gly  Phe  Met  Gln  Gln  Gly  Ser  Glu
                    580                      585                      590

ATC  ATG  CCC  CGG  GCG  CTG  TCC  ACG  CGC  TGT  GTC  AGC  GGA  GTC  TGG  TGG                    2050
Ile  Met  Pro  Arg  Ala  Leu  Ser  Thr  Arg  Cys  Val  Ser  Gly  Val  Trp  Trp
               595                      600                      605

GCC  TTC  ACC  TTG  ATC  ATC  ATC  TCC  TCC  TAC  ACG  GCC  AAC  CTG  GCC  GCC                    2098
Ala  Phe  Thr  Leu  Ile  Ile  Ile  Ser  Ser  Tyr  Thr  Ala  Asn  Leu  Ala  Ala
          610                      615                      620

TTC  CTC  ACC  GTG  CAG  CGC  ATG  GAG  GTG  CCT  GTG  GAG  TCG  GCC  GAT  GAC                    2146
Phe  Leu  Thr  Val  Gln  Arg  Met  Glu  Val  Pro  Val  Glu  Ser  Ala  Asp  Asp
     625                      630                      635

CTG  GCA  GAT  CAG  ACC  AAC  ATC  GAG  TAT  GGC  ACC  ATC  CAC  GCC  GGC  TCC                    2194
Leu  Ala  Asp  Gln  Thr  Asn  Ile  Glu  Tyr  Gly  Thr  Ile  His  Ala  Gly  Ser
640                      645                      650                      655

ACC  ATG  ACC  TTC  TTC  CAG  AAT  TCA  CGG  TAC  CAA  ACG  TAC  CAG  CGC  ATG                    2242
Thr  Met  Thr  Phe  Phe  Gln  Asn  Ser  Arg  Tyr  Gln  Thr  Tyr  Gln  Arg  Met
                    660                      665                      670

TGG  AAC  TAC  ATG  CAG  TCG  AAG  CAG  CCC  AGC  GTG  TTC  GTC  AAG  AGC  ACA                    2290
Trp  Asn  Tyr  Met  Gln  Ser  Lys  Gln  Pro  Ser  Val  Phe  Val  Lys  Ser  Thr
               675                      680                      685

GAA  GAG  GGC  ATT  GCC  GCC  GTC  CTC  AAC  TCC  CGC  TAC  GCC  TTC  CTG  CTC                    2338
Glu  Glu  Gly  Ile  Ala  Ala  Val  Leu  Asn  Ser  Arg  Tyr  Ala  Phe  Leu  Leu
          690                      695                      700

GAG  TCC  ACC  ATG  AAC  GAA  TAC  CAC  CGG  CGC  CTC  AAC  TGC  AAC  CTC  ACC                    2386
Glu  Ser  Thr  Met  Asn  Glu  Tyr  His  Arg  Arg  Leu  Asn  Cys  Asn  Leu  Thr
     705                      710                      715

CAG  ATC  GGG  GGA  CTC  CTC  GAC  ACC  AAG  GGC  TAC  GGC  ATT  GGC  ATG  CCG                    2434
Gln  Ile  Gly  Gly  Leu  Leu  Asp  Thr  Lys  Gly  Tyr  Gly  Ile  Gly  Met  Pro
720                      725                      730                      735

CTG  GGC  TCC  CCG  TTC  CGG  GAT  GAG  ATC  ACA  CTG  GCC  ATC  CTG  CAG  CTT                    2482
Leu  Gly  Ser  Pro  Phe  Arg  Asp  Glu  Ile  Thr  Leu  Ala  Ile  Leu  Gln  Leu
                    740                      745                      750

CAG  GAG  AAC  AAC  CGG  CTG  GAG  ATC  CTG  AAG  CGC  AAG  TGG  TGG  GAG  GGG                    2530
Gln  Glu  Asn  Asn  Arg  Leu  Glu  Ile  Leu  Lys  Arg  Lys  Trp  Trp  Glu  Gly
               755                      760                      765

GGC  CGG  TGC  CCC  AAG  GAG  GAG  GAC  CAT  CGA  GCT  AAA  GGT  TTG  GGC  ATG                    2578
Gly  Arg  Cys  Pro  Lys  Glu  Glu  Asp  His  Arg  Ala  Lys  Gly  Leu  Gly  Met
          770                      775                      780

GAG  AAC  ATT  GGT  GGC  ATT  TTT  ATC  GTG  CTC  ATC  TGT  GGC  CTC  ATC  ATT                    2626
Glu  Asn  Ile  Gly  Gly  Ile  Phe  Ile  Val  Leu  Ile  Cys  Gly  Leu  Ile  Ile
     785                      790                      795

GCT  GTC  TTC  GTG  GCG  GTC  ATG  GAA  TTC  ATA  TGG  TCC  ACA  CGG  AGG  TCA                    2674
Ala  Val  Phe  Val  Ala  Val  Met  Glu  Phe  Ile  Trp  Ser  Thr  Arg  Arg  Ser
800                      805                      810                      815

GCT  GAG  TCC  GAG  GAG  GTG  TCG  GTG  TGC  CAG  GAG  ATG  CTG  CAG  GAG  CTG                    2722
Ala  Glu  Ser  Glu  Glu  Val  Ser  Val  Cys  Gln  Glu  Met  Leu  Gln  Glu  Leu
                    820                      825                      830

CGC  CAC  GCC  GTT  TCT  TGC  CGC  AAG  ACG  TCG  CGT  TCC  CGC  GGC  GCC  CGA                    2770
Arg  His  Ala  Val  Ser  Cys  Arg  Lys  Thr  Ser  Arg  Ser  Arg  Arg  Arg  Arg
               835                      840                      845

CGC  CCG  GGC  GGC  CCG  AGC  CGG  GCC  CTG  CTG  TCA  CTG  CGC  GCG  GTC  CGC                    2818
Arg  Pro  Gly  Gly  Pro  Ser  Arg  Ala  Leu  Leu  Ser  Leu  Arg  Ala  Val  Arg
          850                      855                      860

GAG  ATG  CGC  CTC  AGC  AAC  GGC  AAG  CTC  TAC  TCG  GCC  GGC  GCG  GGC  GGG                    2866
```

```
Glu  Met  Arg  Leu  Ser  Asn  Gly  Lys  Leu  Tyr  Ser  Ala  Gly  Ala  Gly  Gly
     865                      870                      875

GAT  GCG  GGC  AGC  GCG  CAC  GGG  GGC  CCG  CAG  CGC  CTC  CTG  GAC  GAC  CCG      2914
Asp  Ala  Gly  Ser  Ala  His  Gly  Gly  Pro  Gln  Arg  Leu  Leu  Asp  Asp  Pro
880                      885                      890                      895

GGG  CCC  CCC  AGC  GGA  GCC  CGA  CCC  GCC  GCC  CCC  ACC  CCC  TGC  ACC  CAC      2962
Gly  Pro  Pro  Ser  Gly  Ala  Arg  Pro  Ala  Ala  Pro  Thr  Pro  Cys  Thr  His
                    900                      905                      910

GTG  CGC  GTC  TGC  CAG  GAG  TGC  CGG  CGC  ATC  CAG  GCG  CTG  CGG  GCC  TCG      3010
Val  Arg  Val  Cys  Gln  Glu  Cys  Arg  Arg  Ile  Gln  Ala  Leu  Arg  Ala  Ser
               915                      920                      925

GGG  GCC  GGC  GCG  CCT  CCG  CGT  GGC  CTG  GGC  GTC  CCC  GCC  GAA  GCC  ACC      3058
Gly  Ala  Gly  Ala  Pro  Pro  Arg  Gly  Leu  Gly  Val  Pro  Ala  Glu  Ala  Thr
          930                      935                      940

AGC  CCG  CCC  CGG  CCG  CGG  CCT  GGC  CCC  GCC  GGC  CCC  CGG  GAG  CTG  GCG      3106
Ser  Pro  Pro  Arg  Pro  Arg  Pro  Gly  Pro  Ala  Gly  Pro  Arg  Glu  Leu  Ala
     945                      950                      955

GAG  CAC  GAG  TGACCACGGG  CGGGGCTGTG  CGGGCGCCCG  GACTGACCGA                        3155
Glu  His  Glu
960

AGGGACGGGG  CCCGCCCCAG  GCCCCAGCAG  TCTCCGCTCC  CGCAGCGGGC  GCGGGACAGG               3215

ACTTGTGCGC  CGGCGCCCCG  GACGCCGCGA  TTTTGCCTTT  GGTTCCCCGC  GAAGTCCGAG               3275

GCCTGGCTCT  GGAGCCCGCC  TGCGCCCCCC  AGTGGACTCG  CGAGAGGGTG  CCGCGGGCGA               3335

GAAGGGCGCA  GGAACCGAGG  ACTCCAGGGG  CTGGGGACTT  CGGGGGCGGC  TCTGGGAAGC               3395

GGAAAGCAGT  CAGCGGAGAG  GACCCCATTC  TGGGACTGCT  CAGGCTCCCC  AAGACTTGAC               3455

GCAGCCCCCC  ACGCTTCTGA  GGTGGGGAGG  GCCTCTGGAC  AGATGGGTGT  CCCCTGGTGC               3515

CCCTCCACTC  TTCTCTTCCT  CTCTTTTTTG  GGGGAGAAA   CCTCGGAATT  TCTATGAGAC               3575

CTCCCCCAGG  GAGGGGGTCA  GTTGGGCCCC  CATCCCTCCC  CTTGCCACAT  CGCAGCCCCT               3635

GTTGGAATAA  AAAAAAGAAC  AAAAGGGGAA  AAAAAAAAA   AAAAAAAAA   AAAGGAATTC               3695
```

( 2 ) INFORMATION FOR SEQ ID NO:2:

( i ) SEQUENCE CHARACTERISTICS:
        ( A ) LENGTH: 980 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Pro  Ala  Glu  Leu  Leu  Leu  Leu  Ile  Val  Ala  Phe  Ala  Ser  Pro
-18            -15                 -10                      -5

Ser  Cys  Gln  Val  Leu  Ser  Ser  Leu  Arg  Met  Ala  Ala  Ile  Leu  Asp  Asp
          1              5                        10

Gln  Thr  Val  Cys  Gly  Arg  Gly  Glu  Arg  Leu  Ala  Leu  Ala  Leu  Ala  Arg
15                  20                       25                           30

Glu  Gln  Ile  Asn  Gly  Ile  Ile  Glu  Val  Pro  Ala  Lys  Ala  Arg  Val  Glu
                35                       40                       45

Val  Asp  Ile  Phe  Glu  Leu  Gln  Arg  Asp  Ser  Gln  Tyr  Glu  Thr  Thr  Asp
               50                       55                       60

Thr  Met  Cys  Gln  Ile  Leu  Pro  Lys  Gly  Val  Val  Ser  Val  Leu  Gly  Pro
          65                  70                       75

Ser  Ser  Ser  Pro  Ala  Ser  Ala  Ser  Thr  Val  Ser  His  Ile  Cys  Gly  Glu
          80                  85                       90

Lys  Glu  Ile  Pro  His  Ile  Lys  Val  Gly  Pro  Glu  Glu  Thr  Pro  Arg  Leu
95                  100                      105                          110
```

```
Gln Tyr Leu Arg Phe Ala Ser Val Ser Leu Tyr Pro Ser Asn Glu Asp
                115                 120                 125
Val Ser Leu Ala Val Ser Arg Ile Leu Lys Ser Phe Asn Tyr Pro Ser
            130                 135                 140
Ala Ser Leu Ile Cys Ala Lys Ala Glu Cys Leu Leu Arg Leu Glu Glu
            145                 150                 155
Leu Val Arg Gly Phe Leu Ile Ser Lys Glu Thr Leu Ser Val Arg Met
    160                 165                 170
Leu Asp Asp Ser Arg Asp Pro Thr Pro Leu Leu Lys Glu Ile Arg Asp
175                 180                 185                 190
Asp Lys Val Ser Thr Ile Ile Asp Ala Asn Ala Ser Ile Ser His
                195                 200                 205
Leu Ile Leu Arg Lys Ala Ser Glu Leu Gly Met Thr Ser Ala Phe Tyr
            210                 215                 220
Lys Tyr Ile Leu Thr Thr Met Asp Phe Pro Ile Leu His Leu Asp Gly
        225                 230                 235
Ile Val Glu Asp Ser Ser Asn Ile Leu Gly Phe Ser Met Phe Asn Thr
    240                 245                 250
Ser His Pro Phe Tyr Pro Glu Phe Val Arg Ser Leu Asn Met Ser Trp
255                 260                 265                 270
Arg Glu Asn Cys Glu Ala Ser Thr Tyr Leu Gly Pro Ala Leu Ser Ala
            275                 280                 285
Ala Leu Met Phe Asp Ala Val His Val Val Ser Ala Val Arg Glu
        290                 295                 300
Leu Asn Arg Ser Gln Glu Ile Gly Val Lys Pro Leu Ala Cys Thr Ser
        305                 310                 315
Ala Asn Ile Trp Pro His Gly Thr Ser Leu Met Asn Tyr Leu Arg Met
    320                 325                 330
Val Glu Tyr Asp Gly Leu Thr Gly Arg Val Glu Phe Asn Ser Lys Gly
335                 340                 345                 350
Gln Arg Thr Asn Tyr Thr Leu Arg Ile Leu Glu Lys Ser Arg Gln Gly
            355                 360                 365
His Arg Glu Ile Gly Val Trp Tyr Ser Asn Arg Thr Leu Ala Met Asn
        370                 375                 380
Ala Thr Thr Leu Asp Ile Asn Leu Ser Gln Thr Leu Ala Asn Lys Thr
    385                 390                 395
Leu Val Val Thr Thr Ile Leu Glu Asn Pro Tyr Val Met Arg Arg Pro
    400                 405                 410
Asn Phe Gln Gly Leu Ser Gly Asn Glu Arg Phe Glu Gly Phe Cys Val
415                 420                 425                 430
Asp Met Leu Arg Glu Leu Ala Glu Leu Leu Pro Phe Pro Tyr Arg Leu
            435                 440                 445
Arg Leu Val Glu Asp Gly Leu Tyr Gly Ala Pro Glu Pro Asn Gly Ser
        450                 455                 460
Trp Thr Gly Met Val Gly Glu Leu Ile Asn Arg Lys Ala Asp Leu Ala
    465                 470                 475
Val Ala Ala Phe Thr Ile Thr Ala Glu Arg Glu Lys Val Ile Asp Phe
    480                 485                 490
Ser Lys Pro Phe Met Thr Leu Gly Ile Ser Ile Leu Tyr Arg Val His
495                 500                 505                 510
Met Gly Arg Lys Pro Gly Tyr Phe Ser Phe Leu Asp Pro Phe Ser Pro
            515                 520                 525
Ala Val Trp Leu Phe Met Leu Leu Ala Tyr Leu Ala Val Ser Cys Val
```

|   |   |   |   |   |   |   |   |   |   |   |   |   |   |   |
|---|---|---|---|---|---|---|---|---|---|---|---|---|---|---|
|   |   |   |   | 530 |   |   |   |   | 535 |   |   |   |   | 540 |
| Leu | Phe | Leu | Ala | Ala | Arg | Leu | Ser | Pro | Tyr | Glu | Trp | Tyr | Asn | Pro | His |
|   |   |   | 545 |   |   |   | 550 |   |   |   | 555 |   |   |   |
| Pro | Cys | Leu | Arg | Ala | Arg | Pro | His | Ile | Leu | Glu | Asn | Gln | Tyr | Thr | Leu |
|   |   | 560 |   |   |   | 565 |   |   |   | 570 |   |   |   |   |
| Gly | Asn | Ser | Leu | Trp | Phe | Pro | Val | Gly | Gly | Phe | Met | Gln | Gln | Gly | Ser |
| 575 |   |   |   |   | 580 |   |   |   |   | 585 |   |   |   |   | 590 |
| Glu | Ile | Met | Pro | Arg | Ala | Leu | Ser | Thr | Arg | Cys | Val | Ser | Gly | Val | Trp |
|   |   |   |   | 595 |   |   |   |   | 600 |   |   |   |   | 605 |   |
| Trp | Ala | Phe | Thr | Leu | Ile | Ile | Ile | Ser | Ser | Tyr | Thr | Ala | Asn | Leu | Ala |
|   |   |   | 610 |   |   |   |   | 615 |   |   |   |   | 620 |   |   |
| Ala | Phe | Leu | Thr | Val | Gln | Arg | Met | Glu | Val | Pro | Val | Glu | Ser | Ala | Asp |
|   |   |   | 625 |   |   |   |   | 630 |   |   |   |   | 635 |   |   |
| Asp | Leu | Ala | Asp | Gln | Thr | Asn | Ile | Glu | Tyr | Gly | Thr | Ile | His | Ala | Gly |
|   | 640 |   |   |   |   | 645 |   |   |   |   | 650 |   |   |   |   |
| Ser | Thr | Met | Thr | Phe | Phe | Gln | Asn | Ser | Arg | Tyr | Gln | Thr | Tyr | Gln | Arg |
| 655 |   |   |   |   | 660 |   |   |   |   | 665 |   |   |   |   | 670 |
| Met | Trp | Asn | Tyr | Met | Gln | Ser | Lys | Gln | Pro | Ser | Val | Phe | Val | Lys | Ser |
|   |   |   |   | 675 |   |   |   |   | 680 |   |   |   |   | 685 |   |
| Thr | Glu | Glu | Gly | Ile | Ala | Ala | Val | Leu | Asn | Ser | Arg | Tyr | Ala | Phe | Leu |
|   |   |   | 690 |   |   |   |   | 695 |   |   |   |   | 700 |   |   |
| Leu | Glu | Ser | Thr | Met | Asn | Glu | Tyr | His | Arg | Arg | Leu | Asn | Cys | Asn | Leu |
|   |   | 705 |   |   |   |   | 710 |   |   |   |   | 715 |   |   |   |
| Thr | Gln | Ile | Gly | Gly | Leu | Leu | Asp | Thr | Lys | Gly | Tyr | Gly | Ile | Gly | Met |
|   | 720 |   |   |   |   | 725 |   |   |   |   | 730 |   |   |   |   |
| Pro | Leu | Gly | Ser | Pro | Phe | Arg | Asp | Glu | Ile | Thr | Leu | Ala | Ile | Leu | Gln |
| 735 |   |   |   |   | 740 |   |   |   |   | 745 |   |   |   |   | 750 |
| Leu | Gln | Glu | Asn | Asn | Arg | Leu | Glu | Ile | Leu | Lys | Arg | Lys | Trp | Trp | Glu |
|   |   |   |   | 755 |   |   |   |   | 760 |   |   |   |   | 765 |   |
| Gly | Gly | Arg | Cys | Pro | Lys | Glu | Glu | Asp | His | Arg | Ala | Lys | Gly | Leu | Gly |
|   |   |   | 770 |   |   |   |   | 775 |   |   |   |   | 780 |   |   |
| Met | Glu | Asn | Ile | Gly | Gly | Ile | Phe | Ile | Val | Leu | Ile | Cys | Gly | Leu | Ile |
|   |   | 785 |   |   |   |   | 790 |   |   |   |   | 795 |   |   |   |
| Ile | Ala | Val | Phe | Val | Ala | Val | Met | Glu | Phe | Ile | Trp | Ser | Thr | Arg | Arg |
|   | 800 |   |   |   |   | 805 |   |   |   |   | 810 |   |   |   |   |
| Ser | Ala | Glu | Ser | Glu | Glu | Val | Ser | Val | Cys | Gln | Glu | Met | Leu | Gln | Glu |
| 815 |   |   |   |   | 820 |   |   |   |   | 825 |   |   |   |   | 830 |
| Leu | Arg | His | Ala | Val | Ser | Cys | Arg | Lys | Thr | Ser | Arg | Ser | Arg | Arg | Arg |
|   |   |   |   | 835 |   |   |   |   | 840 |   |   |   |   | 845 |   |
| Arg | Arg | Pro | Gly | Gly | Pro | Ser | Arg | Ala | Leu | Leu | Ser | Leu | Arg | Ala | Val |
|   |   |   | 850 |   |   |   |   | 855 |   |   |   |   | 860 |   |   |
| Arg | Glu | Met | Arg | Leu | Ser | Asn | Gly | Lys | Leu | Tyr | Ser | Ala | Gly | Ala | Gly |
|   |   | 865 |   |   |   |   | 870 |   |   |   |   | 875 |   |   |   |
| Gly | Asp | Ala | Gly | Ser | Ala | His | Gly | Gly | Pro | Gln | Arg | Leu | Leu | Asp | Asp |
|   | 880 |   |   |   |   | 885 |   |   |   |   | 890 |   |   |   |   |
| Pro | Gly | Pro | Pro | Ser | Gly | Ala | Arg | Pro | Ala | Ala | Pro | Thr | Pro | Cys | Thr |
| 895 |   |   |   |   | 900 |   |   |   |   | 905 |   |   |   |   | 910 |
| His | Val | Arg | Val | Cys | Gln | Glu | Cys | Arg | Arg | Ile | Gln | Ala | Leu | Arg | Ala |
|   |   |   |   | 915 |   |   |   |   | 920 |   |   |   |   | 925 |   |
| Ser | Gly | Ala | Gly | Ala | Pro | Pro | Arg | Gly | Leu | Gly | Val | Pro | Ala | Glu | Ala |
|   |   |   | 930 |   |   |   |   | 935 |   |   |   |   | 940 |   |   |
| Thr | Ser | Pro | Pro | Arg | Pro | Arg | Pro | Gly | Pro | Ala | Gly | Pro | Arg | Glu | Leu |
|   |   |   | 945 |   |   |   |   | 950 |   |   |   |   | 955 |   |   |

Ala Glu His Glu
960

( 2 ) INFORMATION FOR SEQ ID NO:3:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:3:

GGGGTTTAAG CTTGGCCCTG TGGACTGCCC TCTCC 35

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:4:

GAAGTCCATG GTGGTGAGGA TG 22

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:5:

CATCCTCACC ACCATGGACT TC 22

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:6:

TCCGGTTGAT GAGCTCGCCA AC 22

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:7:

GTTGGCGAGC TCATCAACCG GA    22

( 2 ) INFORMATION FOR SEQ ID NO:8:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:8:

GCCCAGCGGC ATGCCAATGC CG    22

( 2 ) INFORMATION FOR SEQ ID NO:9:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:9:

CGGCATTGGC ATGCCGCTGG GC    22

( 2 ) INFORMATION FOR SEQ ID NO:10:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:10:

GGGGTTTAAG CTTATTCCAA CAGGGGCTGC GATGT    35

( 2 ) INFORMATION FOR SEQ ID NO:11:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( x i ) SEQUENCE DESCRIPTION: SEQ ID NO:11:

AGCTTGCGGC CGC    13

( 2 ) INFORMATION FOR SEQ ID NO:12:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( i v ) ANTI-SENSE: YES ( x i ) SEQUENCE DESCRIPTION: SEQ ID NO:12:

GCGGCCGCA                                                                                                                9

( 2 ) INFORMATION FOR SEQ ID NO:13:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

Met Val Gly Glu Leu Ile Asn Arg Gln Lys Ala Asp Leu Ala Val Ala
1               5                   10                  15

( 2 ) INFORMATION FOR SEQ ID NO:14:

( i ) SEQUENCE CHARACTERISTICS:
        ( A ) LENGTH: 47 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:14:

ATGGTTGGCG AGCTCATCAA CCGGCAGAAG GCAGACCTGG CTGTGGC                                                     47

( 2 ) INFORMATION FOR SEQ ID NO:15:

( i ) SEQUENCE CHARACTERISTICS:
        ( A ) LENGTH: 24 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:15:

ATGGTTGGCG AGCTCATCAA CCGG                                                                              24

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:16:

AAGGCAGACC TGGCTGTGGC C                                                                                 21

( 2 ) INFORMATION FOR SEQ ID NO:17:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

Met Val Gly Glu Leu Ile Asn Arg
1               5

( 2 ) INFORMATION FOR SEQ ID NO:18:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

```
Lys Ala Asp Leu Ala Val Ala
 1               5
```

( 2 ) INFORMATION FOR SEQ ID NO:19:

( i ) SEQUENCE CHARACTERISTICS:
        ( A ) LENGTH: 100 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:19:

```
CTGCCAGGTG CTCTCATCAC TGCGCATGGC TGCAATCCTG GATGATCAGA CAGTGTGTGG      60

CCGCGGTGAG CGTCTGGCCT TGGCCTTGGC CCGGGAGCAG                          100
```

( 2 ) INFORMATION FOR SEQ ID NO:20:

( i ) SEQUENCE CHARACTERISTICS:
        ( A ) LENGTH: 79 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:20:

```
GGATGAGGCA CAAGAATCAC TTGGACCGGG AGGCAGGAGT TGCAGTGAGC GTCTGGCCTT     60

GGCCTTGGCC CGGGAGCAG                                                 79
```

( 2 ) INFORMATION FOR SEQ ID NO:21:

( i ) SEQUENCE CHARACTERISTICS:
        ( A ) LENGTH: 88 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:21:

```
Met Pro Ala Glu Leu Leu Leu Leu Ile Val Ala Phe Ala Ser Pro
 1               5                  10                  15

Ser Cys Gln Val Leu Ser Ser Leu Arg Met Ala Ala Ile Leu Asp Asp
                 20              25                  30

Gln Thr Val Cys Gly Arg Gly Glu Arg Leu Ala Leu Ala Leu Ala Arg
             35              40              45

Glu Gln Ile Asn Gly Ile Ile Glu Val Pro Ala Lys Ala Arg Val Glu
         50              55              60

Val Asp Ile Phe Glu Leu Gln Arg Asp Ser Gln Tyr Glu Thr Thr Asp
 65                  70              75                  80

Thr Met Cys Gln Ile Leu Pro Lys
                 85
```

( 2 ) INFORMATION FOR SEQ ID NO:22:

( i ) SEQUENCE CHARACTERISTICS:
( A ) LENGTH: 64 amino acids
( B ) TYPE: amino acid
( D ) TOPOLOGY: linear ( i i ) MOLECULE TYPE: peptide ( x i ) SEQUENCE DESCRIPTION: SEQ ID NO:22:

Asp Glu Ala Gln Glu Ser Leu Gly Pro Gly Gly Arg Ser Cys Ser Glu
1               5               10              15

Arg Leu Ala Leu Ala Leu Ala Arg Glu Gln Ile Asn Gly Ile Ile Glu
            20              25                  30

Val Pro Ala Lys Ala Arg Val Glu Val Asp Ile Phe Glu Leu Gln Arg
        35              40              45

Asp Ser Gln Tyr Glu Thr Thr Asp Thr Met Cys Gln Ile Leu Pro Lys
    50              55              60

( 2 ) INFORMATION FOR SEQ ID NO:23:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( i i ) MOLECULE TYPE: Other nucleic acid;
( A ) DESCRIPTION: Synthetic DNA oligonucleotide ( x i ) SEQUENCE DESCRIPTION: SEQ ID NO:23:

GGGGTTTAAG CTTGAGCGTC GTCCTCTTCC TGGT                    34

( 2 ) INFORMATION FOR SEQ ID NO:24:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( i i ) MOLECULE TYPE: Other nucleic acid;
( A ) DESCRIPTION: Synthetic DNA oligonucleotide ( x i ) SEQUENCE DESCRIPTION: SEQ ID NO:24:

GGGGTTTAAG CTTGTGAAGA ACCACCAGAC GCCG                    34